United States Patent
Dixit et al.

(10) Patent No.: US 9,679,011 B2
(45) Date of Patent: *Jun. 13, 2017

(54) PERFORMING SEQUENCE ANALYSIS AS A RELATIONAL JOIN

(71) Applicant: IBM International Group B.V., Amsterdam (NL)

(72) Inventors: Sanjay G. Dixit, Los Altos, CA (US); Venkannababu Tammisetti, Shrewsbury, MA (US); Barry M. Zane, La Jolla, CA (US)

(73) Assignee: IBM INTERNATIONAL GROUP B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,834

(22) Filed: May 19, 2016

(65) Prior Publication Data

US 2016/0267136 A1  Sep. 15, 2016

Related U.S. Application Data

(63) Continuation of application No. 14/879,140, filed on Oct. 9, 2015, which is a continuation of application
(Continued)

(51) Int. Cl.
G06F 17/30 (2006.01)
G06F 19/00 (2011.01)
G06F 19/22 (2011.01)

(52) U.S. Cl.
CPC .. *G06F 17/30466* (2013.01); *G06F 17/30421* (2013.01); *G06F 17/30471* (2013.01); *G06F 17/30498* (2013.01); *G06F 17/30548* (2013.01); *G06F 19/3443* (2013.01); *G06F 19/22* (2013.01); *Y10S 707/99931* (2013.01)

(58) Field of Classification Search
None
See application file for complete search history.

(56) References Cited

U.S. PATENT DOCUMENTS

| 4,497,039 A | 1/1985 | Kitakami et al. |
| 5,701,256 A | 12/1997 | Marr et al. |

(Continued)

FOREIGN PATENT DOCUMENTS

| WO | 2005/028627 | 3/2005 |
| WO | 2005/029280 | 3/2005 |

OTHER PUBLICATIONS

Christias, Panagiotis, "GREP (1)" Jan. 2002, GNU project, unixhelp.ed.ac.uk <http://unixhelp.ed.ac.uk/CGI/man-cgi?grep>p. 1-7 with example p. 8.

(Continued)

*Primary Examiner* — Amresh Singh
(74) *Attorney, Agent, or Firm* — Reza Sarbakhsh; Edell, Shapiro & Finnan, LLC

(57) ABSTRACT

A usage model and the underlying technology used to provide sequence analysis as part of a relational database system. Included components include the semantic and syntactic integration of the sequence analysis with an existing query language, the storage methods for the sequence data, and the design of a multipart execution scheme that runs the sequence analysis as part of a potentially larger database join, especially using parallel execution techniques.

20 Claims, 6 Drawing Sheets

Related U.S. Application Data

No. 10/944,281, filed on Sep. 17, 2004, now Pat. No. 9,183,256.

(60) Provisional application No. 60/504,443, filed on Sep. 19, 2003.

(56) References Cited

U.S. PATENT DOCUMENTS

| | | |
|---|---|---|
| 5,717,911 A | 2/1998 | Madrid et al. |
| 5,843,673 A | 12/1998 | Sharpe-Timms |
| 5,873,052 A | 2/1999 | Sharaf |
| 5,884,303 A | 3/1999 | Brown |
| 5,903,893 A | 5/1999 | Kleewein et al. |
| 5,953,727 A | 9/1999 | Maslyn et al. |
| 5,966,712 A | 10/1999 | Sabatini et al. |
| 6,009,271 A | 12/1999 | Whatley |
| 6,223,186 B1 | 4/2001 | Rigault et al. |
| 6,226,628 B1 | 5/2001 | Forbes |
| 6,532,300 B1 | 3/2003 | Noda |
| 6,553,317 B1 | 4/2003 | Lincoln et al. |
| 6,615,222 B2 | 9/2003 | Hornibrook et al. |
| 6,691,109 B2 | 2/2004 | Bjornson et al. |
| 6,917,882 B2 | 7/2005 | Selifonov et al. |
| 7,430,549 B2 | 9/2008 | Zane et al. |
| 7,433,863 B2 | 10/2008 | Zane et al. |
| 7,529,752 B2 | 5/2009 | Hinshaw et al. |
| 7,577,667 B2 | 8/2009 | Hinshaw et al. |
| 7,634,477 B2 | 12/2009 | Hinshaw et al. |
| 7,698,338 B2 | 4/2010 | Hinshaw et al. |
| 7,702,610 B2 | 4/2010 | Zane et al. |
| 7,730,077 B2 | 6/2010 | Hinshaw et al. |
| 8,171,018 B2 | 5/2012 | Zane et al. |
| 8,805,818 B2 | 8/2014 | Zane et al. |
| 9,183,256 B2 | 11/2015 | Zane et al. |
| 2002/0064792 A1 | 5/2002 | Lincoln et al. |
| 2002/0072862 A1 | 6/2002 | Person |
| 2002/0076711 A1 | 6/2002 | Wolffe et al. |
| 2002/0107835 A1 | 8/2002 | Coram et al. |
| 2002/0194646 A1 | 12/2002 | Pogue et al. |
| 2003/0022200 A1 | 1/2003 | Vissing et al. |
| 2003/0140336 A1 | 7/2003 | Kawahito et al. |
| 2003/0190649 A1 | 10/2003 | Aerts et al. |
| 2004/0139400 A1 | 7/2004 | Allam et al. |
| 2004/0249146 A1 | 12/2004 | Shukla et al. |
| 2005/0021533 A1 | 1/2005 | Ayachitula et al. |
| 2005/0091238 A1 | 4/2005 | Zane et al. |
| 2005/0146951 A1 | 7/2005 | Horai et al. |
| 2010/0257537 A1 | 10/2010 | Hinshaw et al. |
| 2016/0110418 A1 | 4/2016 | Dixit et al. |

OTHER PUBLICATIONS

Camp, et al., "High-Throughput Blast—White Paper", Sep. 1998, SGI, 8 pages.

PERFORMING SEQUENCE ANALYSIS AS A RELATIONAL JOIN

RELATED APPLICATIONS

This application claims the benefit of U.S. Provisional Application No. 60/504,443 entitled "PROVIDING SEQUENCE ANALYSIS AS A FORM OF RELATIONAL JOIN ON A RELATIONAL DATABASE SYSTEM", filed on Sep. 19, 2003. The entire teachings of this provisional application is hereby incorporated by reference.

BACKGROUND OF THE INVENTION

It is no secret that the amount and types of information that can be accessed by data processing systems increases at a torrid rate. As the amount of available data increases, so too does the need for technologies that can recognize patterns in data. Indeed, pattern recognition is a recognized research discipline within computer science, devoted to studying the operation and design of systems that recognize patterns in data. It encloses subdisciplines like discriminant analysis, feature extraction, error estimation, cluster analysis (together sometimes called statistical pattern recognition), grammatical inference and parsing (sometimes called syntactical pattern recognition). Important application areas are found in image analysis, character recognition, speech analysis, application areas are found in image analysis, character recognition, speech analysis, man and machine diagnostics, person identification, industrial inspection, and analysis of molecular and/or biological sequences.

One common application of pattern recognition techniques is the analysis of data structures that consist of a sequence (or array) of data values, as compared to other such sequences. Sequence analysis, especially as it pertains to molecular biology, involves searching for similarities between some number of relatively small "needle" or "query" sequences and a typically much larger "haystack" or "subject" sequence. A sequence is a series of values, typically bytes, whose aggregate value has a physical basis. For example, a sequence of amino-acid identifiers bytes may describe a complete protein. Likewise, a sequence of nucleic-acid identifiers may describe the DNA make-up of a chromosome or portion thereof. As another example, in the case of speech analysis, data values in the sequence data may represent the phonemes that make up a series of spoken words.

The most commonly used program for biological sequence analysis is the so-called BLAST (Basic Local Alignment Search Tool), however there are other similar programs. The core BLAST heuristic matching algorithm and a number of programs that use the algorithm are in the public domain and administered by the National Center for Biotechnology Information (NCBI) as described at http://www.ncbi.nih.gov. While the discussion of examples in this document uses the NCBI BLAST integration of biological sequence information as a principal example, it should be understood that the principals discussed herein are suitable for integration with other similar algorithms and/or for other types of data such as speech or image data. Note that the common terms in the biological community are "subject sequence" (to refer to the long sequence) and "query sequence" (to refer to the shorter sequence) rather than "haystack sequence" and "needle sequence", respectively. This document avoids these more standard terms because the word "query", at least when used by itself, has a different meaning in the relational database system art.

A given needle sequence can be similar to a given haystack sequence in several places. Each site of similarity is considered a "local alignment".

Executing a BLAST program for "N" needle sequences against a haystack of "H" sequences results in a description of each of the independent areas of local similarity between every needle and every haystack sequence. Thus, the number of result descriptions can significantly exceed "N×H" values, but the number reported is usually much less because it is limited to those similarities considered statistically significant by the BLAST algorithm.

It is also known that relational databases are used to store and analyze typically large amounts of information. Modern relational databases provide the user with a powerful query language, such as SQL-92 (Structured Query Language, ANSI version 92) to perform analysis and reporting of the data stored in the database system. Data analysis typically involves searching, grouping, counting and relation joining operations.

Molecular sequence analysis requires a large amount of processing resources and the compute time is often excessive as compared to the amount of time desired by the user—sometimes measured in hours or days. Part of this time is typically performed converting sequence formats from stored format to computationally convenient formats and back and also computing other information not ultimately required by the user.

SUMMARY OF THE INVENTION

The present invention is a usage model and the underlying technology used to provide sequence analysis as part of a relational database system. Included components include the semantic and syntactic integration of the sequence analysis with an existing query language, the storage methods for the sequence data, and the design of the execution scheme that runs the sequence analysis as part of a potentially larger database query, especially using parallel execution techniques.

Prior to this invention, relational database systems have not supported sequence analysis. Sequences could be stored in the database, but to be searched by BLAST (or similar program), data elements were required to be exported from the database, converted into a another format, and then operated upon by an independent program that implemented the search algorithm. The resultant data from the search algorithm could then be loaded back into a relational database.

However, the present invention eliminates the export/import and the attendant data conversions and loss of detail information. It provides a much more reliable and higher performance integration of database-based data analysis and sequence analysis. It also reduces the computation of information not directly required by the ultimate result report.

This invention stores the haystack and needle sequences as relational database tables, or more properly, relations—the haystack and/or needle sequences can be the result of previous parts of the query. Thus, neither haystack nor needle is a static materialized "database" definition—they can, for example, be the result of a selection criterion determined at the time of the query such as those people with a specific disease or those proteins involved with a specific metabolic function.

Likewise, the result of the join is directly usable by the next step of the query, such as another join or aggregation—the result set does not need to be materialized.

On parallel-computation systems, this invention also describes a means of distributing the data among the processing and storage units to achieve high performance levels that are roughly proportional to the number of processing units. Specifically, by distributing the haystack sequences approximately evenly across hundreds or thousands of processing units, very large searches are possible in a short amount of time, multiplied by the number of needles sequences. Prior to this invention, parallel computation was performed by replicating the entire haystack in the memory or disk space at each processing unit.

The NCBI Blast algorithm supports a "MegaBlast" convention where the algorithm processes multiple needle sequences against the database, but this requires that the user of the program specify the groups of needle sequences manually, accounting for the memory (and other resource) capabilities of their machine. With this invention, the MegaBlast effect is implicit, more generalized and the needle selection is automatically optimized by the system's query planner.

According to a preferred embodiment, the invention encompasses techniques for sequence analysis where at least one "needle" or "query" sequence and at least one "haystack" or "subject" sequence are stored as a relation. A comparison is then carried out between at least one query sequence and at least one subject sequence as one or more Structured Query Language (SQL) queries. The SQL query(ies) are formulated to include at least one join operation.

As well, in this embodiment, the result of the comparison query can be presented as a relation. In this instance, a number of tuples in the result relation is larger than a multiplicative product of the number of query and subject sequences, to accommodate possible multiple points of similarity.

The SQL query structure permits relational database-like specification for the comparison process. For example, a BLAST type comparison can then be carried out as a relational join of subject sequences against one or more query sequences.

In optional aspects, the SQL query can be formulated with a controls table that specifies parameters of the comparison. In this instance, each of the query sequences can then be compared against each of the subject sequences for each of the parameters of the controls table. Specifically, a first step may involve scanning the controls table as an inner table; scanning the query sequences; and then cross-product joining the resulting records to the inner table, to produce a parameterized query table.

In further aspects of this embodiment of the invention, an auxiliary table may be generated for the resulting relations, for storing statistics and/or histogram data as generated by the comparison.

Implementing the sequence comparison as one or more SQL queries permits query-specific statements to be compiled and dynamically bound at execution time. This further allows for efficient and rapid execution of the comparison, especially in multi-processing architectures, where a central processing unit can serve to compile instructions for other processing units to execute.

Storing comparison results as relations also avoids materialization of sequence data as much as possible, which is another performance enhancement.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF A PREFERRED EMBODIMENT

The invention's preferred implementation is on a parallel relational database system where embedded processors acting as intelligent disks communicate through a hierarchical communications fabric to one or more processors (called the 'hosts') at the root of the communications hierarchy.

Other than the host processors, each embedded processor (called 'Snippet Processing Unit' or 'SPU') consists of a magnetic disk drive, a communications fabric interface, a central processing unit (CPU), random access (RAM) memory and the circuitry required to connect these elements and provide electrical power.

An example parallel relational database system is described in a co-pending U.S. patent application Ser. No. 10/667,128 entitled "Asymmetric Data Streaming Architecture Having Autonomous and Asynchronous Job Processing Unit," filed Sep. 18, 2003 and which is hereby incorporated by reference; although other system architectures may be used.

This hardware system comprises the base for the relational database software system. The interface to the database is thru proprietary and standard interfaces including ODBC and JDBC. These interfaces support a standard relational query processing language—SQL-92.

A. System Level Architecture
First Group Components

The present invention is preferably implemented in a data processing system having at least two "groups" of processing units, in which the individual components of each group are individual network "nodes" within the system. As will be explained in detail below, the the processors in the second group may operate (a) asynchronously, with respect to each other and with respect to processors in the first group and (b) autonomously, in the sense that they can complete assigned tasks without waiting for data from other processors.

Figure 1:
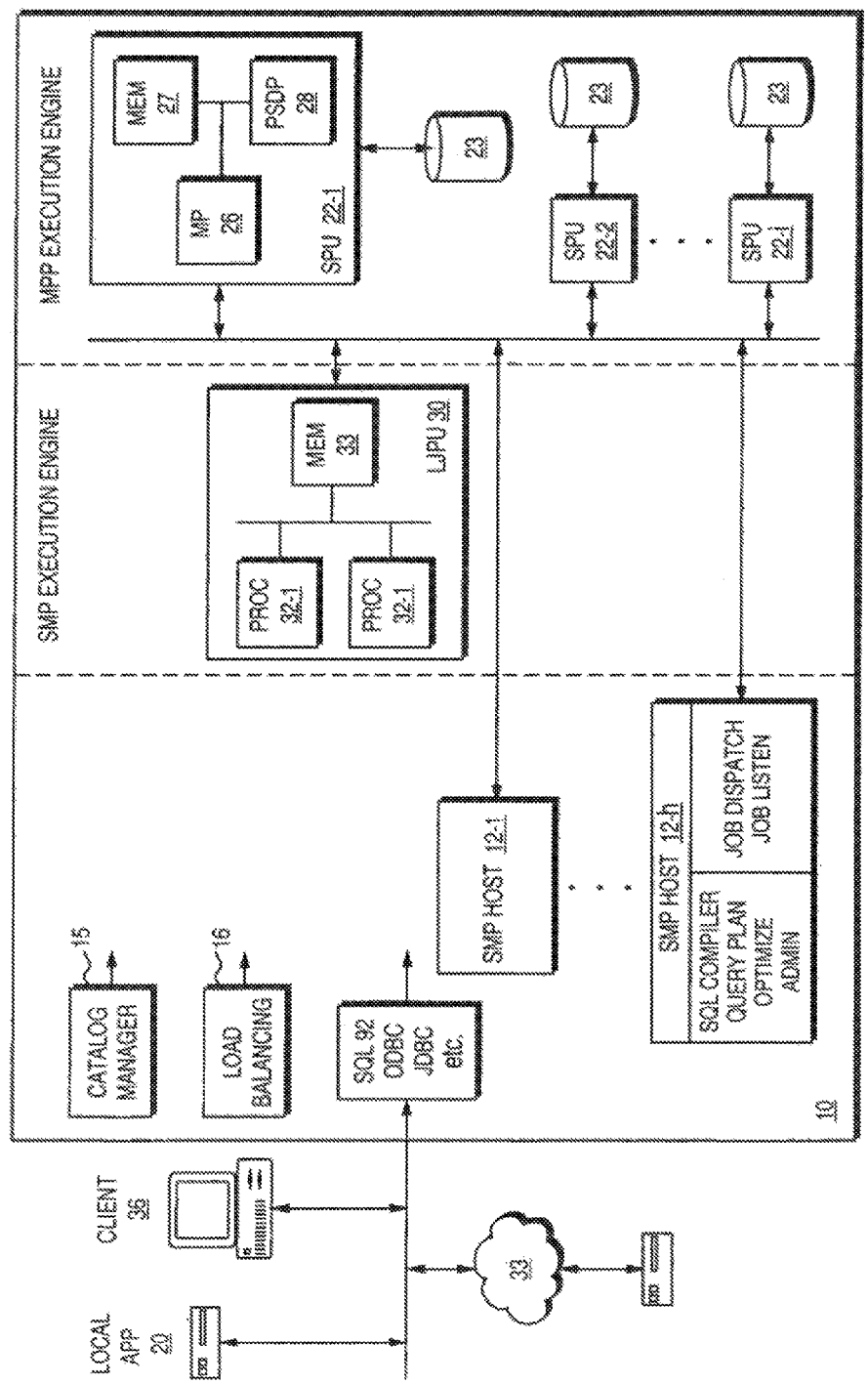
FIG. 1 is a system level block diagram of a sequence comparison system according to the present invention.

As more particularly shown in FIG. 1, the first group 10 consists of one or more SMP "host" computers 12-1, . . . , 12-$h$, each with its own memory, network interface, and local storage (not shown in FIG. 1). Each host 12 runs its own operating system, and typically, but not necessarily, each host 12 uses the same type of operating system as the other hosts 12.

The hosts 12 typically accept queries that are requests for data stored on mass storage devices, such as hard disk drives 23. The requests may originate from any number of applications, typically business intelligence applications, that may be residing on local processors 28 or client computers 36 or separately running application software 30, that may originate through a computer network 33 or locally. Queries are typically provided in a format such as Structured Query Language (SQL), Open DataBase Connectivity (ODBC), Java DataBase Connectivity (JDBC), or the like.

The hosts 12 accept queries that can retrieve, modify, create and/or delete data stored on disk 23 and the schema for such data. The hosts 12 also accept requests to start, commit, and rollback transactions against the data. The hosts 12 also perform typical administrative functions such as reporting on the status of the system 10, start and shutdown operation, backing up the current state of the data, restoring previous states of the data, replicating the data, and performing maintenance operations.

Optionally, there is a load balancing function 11 in front of the host 12 processors, which directs individual transactions to specific host or hosts 12 so as to evenly distribute workload and/or sequence data.

A catalog management component 15 contains descriptions of the fields and layout of data. Catalog management 15 also contains information about which users and applications have which permissions to operate in which ways on which types of records, datasets, and relations. The various hosts 12 interact with catalog management 15 in order to process the requests they receive. In one embodiment, catalog management 15 is embedded within one of the hosts 12, with parts replicated to the other hosts 12 and second group 20 components. As will be understood shortly, the catalog manager is used to provide information to permit the components of the second group 20 to perform filtering functions.

With the exception of their need to consult catalog management 15, the hosts 12 are generally able to respond to requests without having to communicate among themselves. In very rare instances, inter-host 12 communication may occur to resolve a transaction sequencing issue.

Second Group Components

Figure 2:
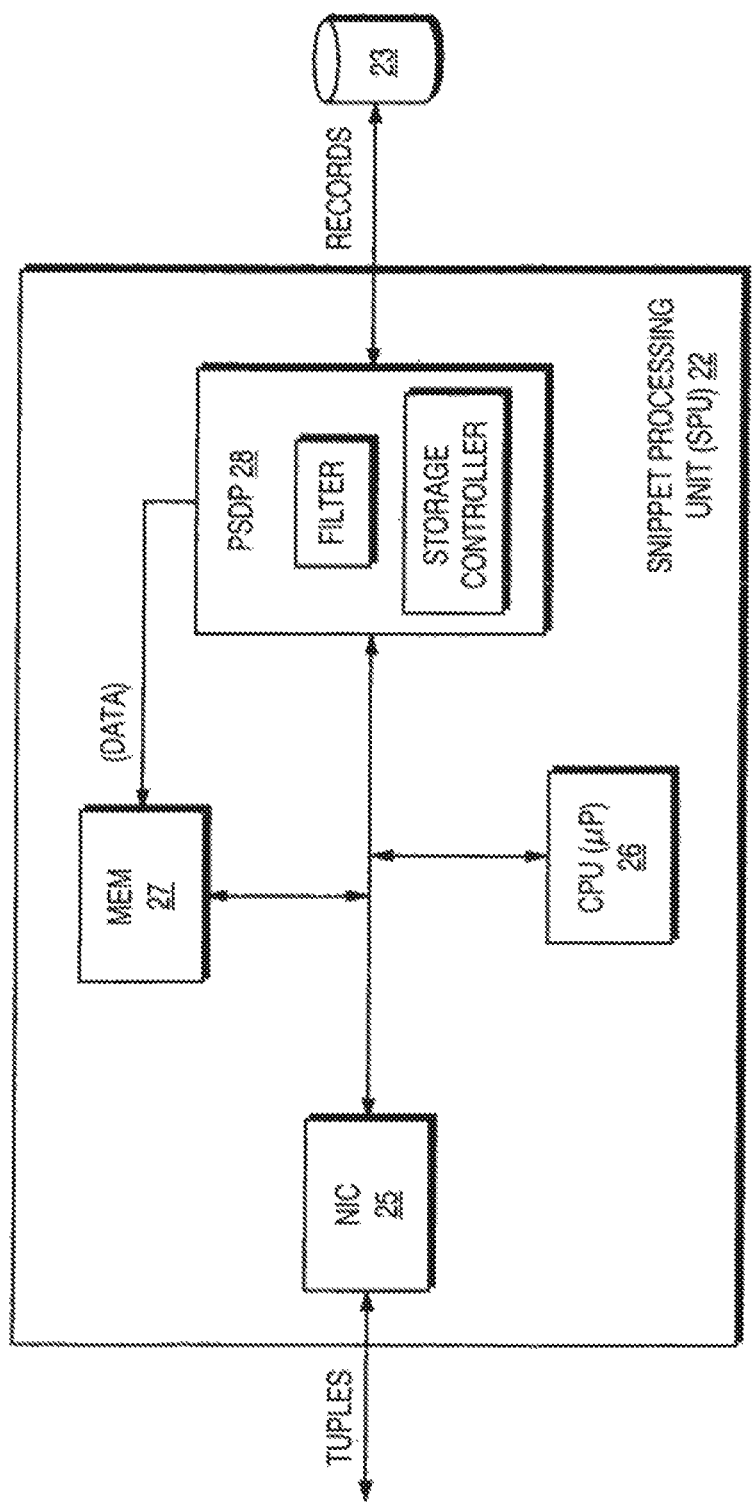
FIG. 2 is a more detailed view of a Snippet Processing Unit (SPU).

The second group 20 of processing units consists of a plurality of "job" or "Snippet" Processing Units (SPUs) 22-1, 22-2, . . . , 22-j. As shown in FIG. 2, each SPU 22 consists of a network interface 25 for receiving requests and delivering replies, a general purpose Central Processing Unit (CPU) 26 such as a microprocessor 26, memory 27, and a Programmable Streaming Record Processor (PSDP) 28. Each SPU 22 runs a multi-tasking schedule-based operating system. Each SPU 22 also has an attached disk 23 and disk controller from which the SPU 22 may read streaming data. In other embodiments, the SPU 22 can receive streaming record data from alternate or additional sources such as other on-board processors or via other network interfaces in place of the disk drives 23.

The SPU 22 accepts and responds to requests from host computers 12 in the first group 10 to process the streaming record-oriented data under its control. These requests are typically "jobs" of a larger SQL query, and are expressed as sequences of primitive operations on an input stream. The primitive operations could be interpreted, but in the preferred embodiment, they are packaged as compiled code that is ready for execution. An exemplary job-based query is described in more detail below.

In addition to processing jobs, a SPU 22 also accepts and responds to requests from hosts for other operations such as:

Start, pre-commit, commit, abort, and recover transactions

Perform mirroring or other replication operations

Start, initialize, reinitialize, stop, and retrieve status information

Create, modify, or delete descriptions of records, indices, views and other metadata Each SPU 22 also accepts and responds to requests from the hosts 12 to:

Perform mirroring or other replication operations

Redistribute data from one SPU to another

Send data local to one SPU to another SPU to help process a query job

Send data to a logging device

Send data to a replication device

Acknowledge the successful completion of an operation requested by another node.

SPU(s) 22 typically use a multi-tasking Operating System (OS) to allow receiving, processing, and reporting the results from multiple jobs in a job queue. In the preferred embodiment, the OS should also support overlapping job execution. To coordinate this, the OS typically is responsible scheduling and prioritizing requests according to a number of factors that are determined in real time. These may include a job priority as assigned by the user and/or host 12, as well as a job's expected impact on the SPU's 22 ideal resources includes the amount of memory, disk, network, and/or I/O queues needed to complete the job. The SPU 22 can also contain software for performing concurrency control, transaction management, recovery and replication of data for which the SPU is responsible.

In the preferred embodiment, SPUs 22 in the second group 20 are not directly visible or accessible to the users of, or the applications that run on, for example, the external clients that present queries to the system 10. The SPUs are an embedded component and maintain significant autonomy and control over their data. A given record (or other data primitive) in the system 10 is thus normally directly accessible to, and processed by only one SPU 22. While SPUs may replicate their records to increase reliability or performance, they do not share responsibility for processing a given record with other SPUs 22 when carrying at a job as part of a query.

A storage manager 320 within each SPU 22 provides autonomous and asynchronous support for other functions such as error checking, creation and deletion of tables, the use and maintenance of indices and views, record insert and delete, mass loading of existing user data among various SPUs, and the like.

Third Group Components

The system architecture exhibits further aspects of asymmetry in that one or more so-called Large Job Processing Units (LJPUs) 30 can also play a part in processing queries. Each LJPU 22 consists of a network interface for receiving job requests and delivering replies, and one or more general purpose Central Processing Units (CPUs) 32-1, . . . , 32-p (each of which may have their own internal memory), as well as a shared memory 38. The CPUs 32 in the LJPUs 30 preferably represent a relatively powerful computing resources, consisting of a relatively high speed processor that has access to relatively large amounts of memory. The LJPUs 30 may be organized as an SMP that share portions of memory 38. The LJPUs may be located in the same SMP cluster as the first processor group.

LJPUs are employed to carry out jobs that are not otherwise suitable or possible to perform on the SPUs 22, such as operations that must be performed on large materialized data sets. This may include sorting, grouping, relational joining and other functions on filtered data, that might not otherwise be possible on a given SPU 22.

The LJPUs 30 also preferably play an important role in other functions. One such function is to serve as an Execution Engine which assists the hosts 12 with coordinating the results from the many jobs that may be running autonomously and asynchronously in the SPUs 22.

LJPU(s) 20 may also typically use a multi-tasking Operating System (OS) to allow receiving, processing, and reporting the results from multiple jobs in a job queue. In the preferred embodiment, the OS should also support overlapping job execution. To coordinate this, the OS typically is responsible scheduling and prioritizing requests according to a number of factors that are determined in real time.

Throughout the system, the components and sub-components are designed to optimize performance through extensive use of streaming operations coupled with tuple set operations. As will be understood shortly most operations are designed to take tuple sets (records or groups of records) as their input and output streams; these operations try not to materialize data, but instead they stream the output to the next operation. As a consequence many operations can be handled as one continuous data flow, whereas in a conventional system, it would be necessary to handle them in various layers.

For instance, a storage layer can be designed as a tuple set manager where (from the view of other SPU processes) it stores and retrieves tuple sets. From the storage layer onward, data is normally handled in tuple sets, providing a consistent, well organized, and easily accessible format for internal operations. This is in contrast to other systems where the storage layer stores and retrieves undifferentiated blocks of data which are later converted to tuple sets by some other downstream process. Another example of the streaming/tuple set architecture is the network layer, which sends and receives tuple sets instead of blocks of data.

A streaming/tuple set operation can be illustrated by tracking a typical dataflow during a load operation. In this example load case, as data is read into a host 12 over TCP/IP network connection 32, that data is parsed, error-checked, and transformed, and the distribution value calculated, all while the specific byte/field is in processor cache, and saved to the internal network output frame buffers as one step.

The result is that the input data is read and transformed in a streaming fashion and converted to network-ready tuple set packets at streaming speed with minimal overhead. Specifically, as each data record is received, it is sent over the internal network 34 to an appropriate SPU 22 (as determined by the a distribution value in a Query Plan). At the SPU 22, the received data is read, converted into an approved storage format, and placed in memory buffers on a record-by-record basis. As memory buffers are filled, a storage layer in the SPU double-checks that the data corresponds to the indicated table, and that the table "owns" the physical space on the disk 23, and then writes that data to the disk 23. Note that during this process, a given byte of data was "touched" only a few times, and that the data was manipulated in tuple sets thereby optimizing performance and reliability.

A second illustration of a streaming tuple set operation is a join/aggregate operation where three joins and one co-located aggregation are performed on SPUs 22, and the results are returned through the host 12 via ODBC to the ODBC client 36 (e.g., Business Objects). In this example, on each of three SPU's, the disk 23 is scanned and data read off the disk through the associated PSDP, which filters records of interest and fields of interest within those records, and places the resulting tuples into a tuple set buffer in SPU memory. As each tuple set buffer is filled, that tuple set is passed through each of three SPU join nodes and the aggregate node in turn. Each time a new key value is received by the aggregate node, the previous aggregate value and associated key value tuple are transformed as necessary per the ODBC request, and placed in the SPU network packet output buffer associated with the requesting host 12. When a network packet output buffer in the SPU is filled, its contents are sent to the host 12, where it is immediately placed in the user-side network buffer and is immediately sent to the ODBC client 36.

Note that, as in the previous example, the data was "touched" only a few times. Because the data was handled in tuple sets, it could be operated on as integral units with very minimal overhead. Because the operations are extremely integrated, mixed operations such as joins, aggregates, output transformation, and network packet creation are all performed while the data is in processor cache memory.

Figure 3:
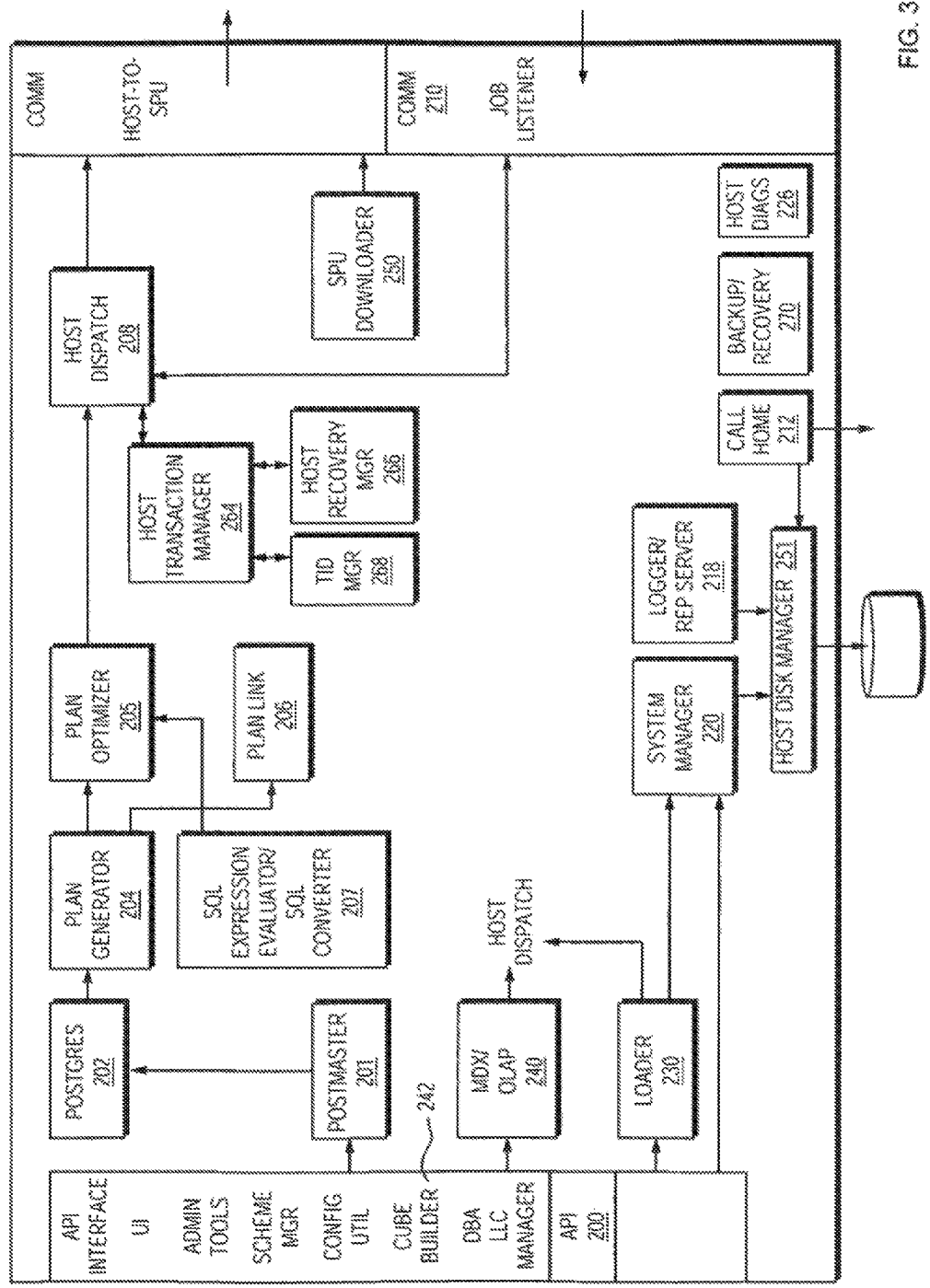
FIG. 3 is a detailed view of software components of a host processing unit.

FIG. 3 is a software component diagram for a host 12. A summary description of the functional blocks and their interactions now follows. This list is intended here to be an a high level generalization how a query is processed into a set of jobs that can then be carried out as synchronously and autonomously by SPUs 22.

Figure 4:
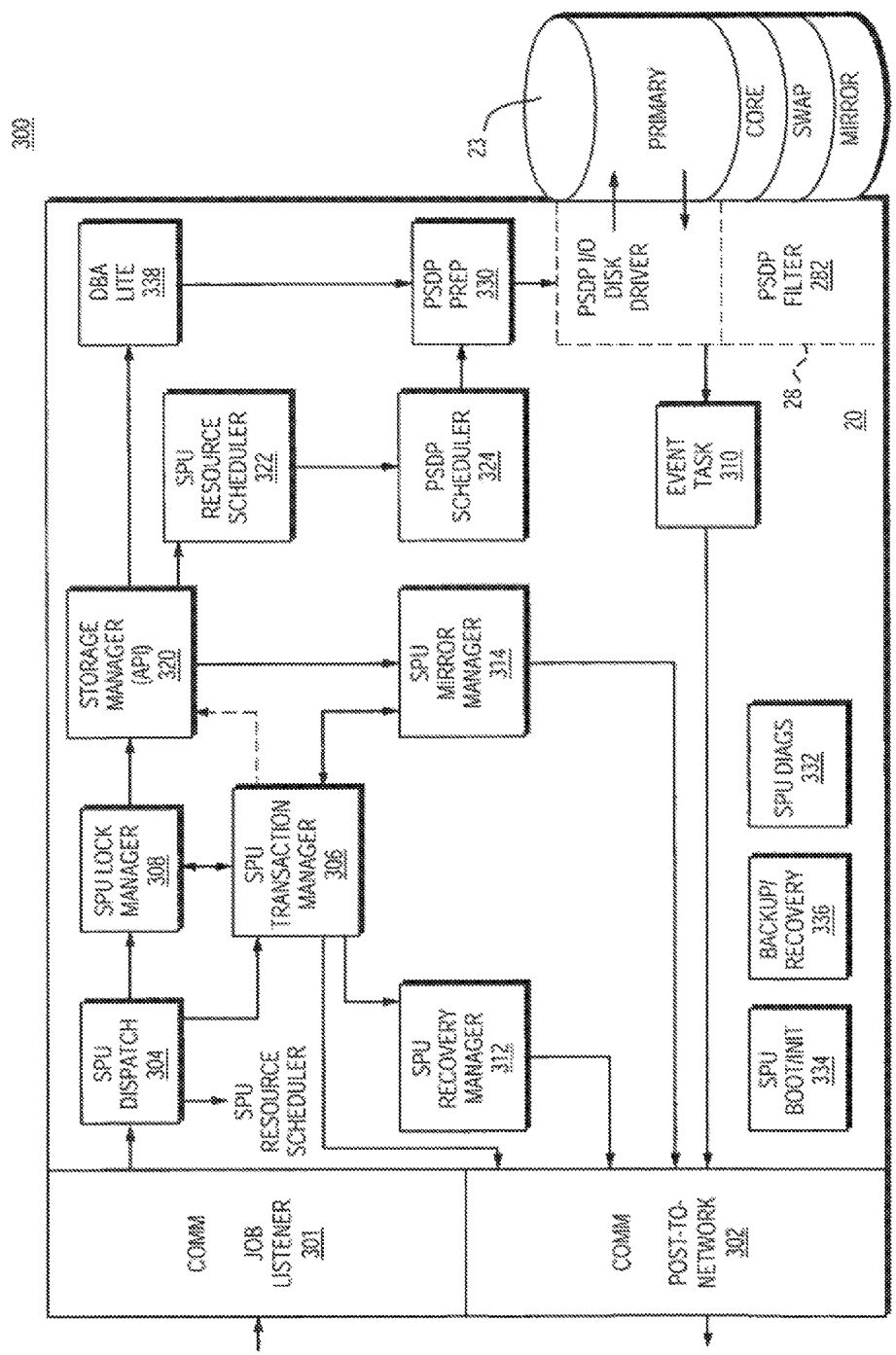
FIG. 4 is a detailed view of Snippet Processing Unit (SPU) software components.

Postmaster 201/Postgres 202
    Serves as Front-end for query processing
    Postmaster 201 accepts requests from user applications via API 200
    Creates an Execution Plan
    May use authentication Plan Generator 204
    Parse/query rewrite/planner—plans how query will be processed.
    Supports SQL-92 DDL/DML
    Supports SQL Functions
    Provides compatibility with Oracle, SQL Server
    Integrated with SQL triggers, stored procedures Plan Optimizer 205
    Cost-based optimizer, with the addition of locale costs which optimizes for most efficient operation/highest level performance
    Indicates which operations will be done within host and which will be done within SPU
    Communicates with Plan Link, providing tips on what filtering should be done within the Programmable Data Streaming Processing ("PSDP") if there are multiple filters that can be done there (more than the PSDP can handle)
    Maintains usage/reference statistics for later index creation, refreshing cluster indices Plan Link 206
    Takes an Execution Plan as input
    Analyzes Execution Plan and splits plan further, identifying what will be done within the PSDP 28, what will be done within the SPU 22 after the PSDP 28 has returned its data to the SPU 22, and what will be done in the Host 12 after the SPU 22 has returned its data SQL Expression Evaluator/SQL Converter 207
    Expression Evaluator
    Creates object code for evaluating given expression to be executed on the Host, SPU, and PSDP based on the expressions, their type, and the capabilities of the installed hardware Host Dispatch 208
  Similar to standard UNIX scheduler/dispatcher
  Queues execution plan and prioritizes based on (a) the plan's priority, history, and expected resource requirements, and (b) available resources and other plans' requirements
  Controls number of jobs being sent to any one SPU 22 or LSPU 30 to avoid SPU/LJPU Scheduler or SPU/LJPU memory overload
  Sends Host jobs to host
  Sends SPUs jobs to be monitored to the Execution Engine 360 in the LJPU.
Communications Layer 210
  Provides communications among the nodes
  Includes Job Listener to await data from nodes
  Uses striping data from a Topology Manager to direct multicast and unicast messages
  Detects non-responsiveness of nodes and communicates with Topology Manager to trigger failover processing
Call Home 212
  Initiates message to a Technical Assistance Center (not shown) to identify failed part and trigger service call or delivery of replacement component (as appropriate given user support level)
  Optionally communicates via SNMP to a defined app to receive a failure indicator and callhome trigger
  Logs error(s)
Logger/Replication Server 218
  Logs transaction plans, messages, failures, etc. to Netezza log in conventional fashion
  Implemented as a standard transaction logger/replication server
System Manager 220
  Defines and maintains SPU/LJPU Configuration information, striping information
  Mirror Master—maintains mirrors info—what SPUs are being mirrored where, maintains SPA data, maintains info on system spares
  Initiates failover processing when informed by Comm layer of a non-communicative SPU—directs mirror of failed SPU to take over as primary and begin copying to designated spare, directs primary of SPU mirrored on failed SPU to copy its data to that same designated spare, to reduce load on mirror of original failed SPU also directs mirror of the primary on that failed SPU's mirror to do double duty and act as new primary until failover copying has been completed
  Communicates to callhome component to initiate replacement process
  Manages system expansion and allows for redistribution of data as appropriate or as requested by user during expansion
  Initiates SPU/LJPU diagnostics when appropriate
  Provides an API to allow client management interface to get configuration data for user display/control
Host Diags 226
  Runs diagnostics on Host as required/requested
Loader 230
  Provides fast loader capability for loading user data onto disks
  Communicates directly to Host Dispatch to load database/insert records
  Communicates with System Manager to get configuration and mirroring data
  Controls index creation on primary (and sets up job to run later to create indices on mirror)
  Supports input via a number of methods (e.g., tab-separated data, backup/recovery)
  Does ETL, converts data from Oracle, SQL Server, DB/2, etc. to the internal data format
MOX/OLAP 240
  Provides OLAP/MDX, ROLAP Engine on Host
  Creates and maintains MOLAP cubes
  Supports multi-user MDX
  Creates Execution Plans for OLAP requests and communicates these directly to Host Dispatch
  Supports metadata writeback
  Provides administrative support for user creation, security
  Access System Catalog through API
Cube Builder User Interface (UI) 242
  Provides interface for defining and managing cubes to be used in OLAP Processing
SPU Downloader 250
  Downloads Firmware to System SPUs 22 at system initiation/boot
  Downloads PSDP 28 and SPU 22 images
  Communicates with System Manager to understand number of SPUs and JPU configurations
  Initializes spares for failover
  Initializes replacements
Host Disk Manager 250
  Manages Host Disk (used for Catalog, Temp Tables, Transaction Log, Netezza Log, Swap space)
Host Transaction Manager 264
  Manages transactions on the host 12
  Controls requests sent to SPUs 22 that will be involved in the transaction
  Provides lock management and deadlock detection
  Initiates abort processing
  Sends state data to Recovery Manager 266
  Sends ID requests to the Transaction I.D.(TID) Manager 268
  Provides transaction IDs and deleted transaction IDs to ensure that disk records are preceded
  Manages catalog requests as transaction requests as required
TID Manager 268
  Provides unique transaction identifiers (TIDs)
  Coordinates with other hosts to avoid generating duplicate TIDs
Host Recovery Manager 266
  Ensures transaction atomicity after component (e.g., SPU) failure
  Maintains journal of transaction state
  Initiates rollback as required
Backup/Recovery 270
  Supports Host side of Backup/Recovery process
  Interfaces with Transaction Manager and SPU Storage Manager
C. SPU Software Components
FIG. 4 is a diagram of the software components of an SPU 22.
Communications Layer 300
  Provides internal communication among nodes
  Includes Job Listener 301 to await requests
  Includes Network Poster 302 to send data when buffer filled, job completed, or at Host request
SPU Dispatch/Scheduler 304
  Receives plan through Communications Layer 300
  Queues Plan
  Schedules/dispatches jobs according to their priority, "fairness" to date, expected resource requirements, and available resources SPU Transaction Manager 306
  Processes changes in transaction state to begin a transaction, pre-commit a transaction, commit a transaction, or abort a transaction
  Handles processing of dependencies among transactions as flagged by the lock manager; broadcasts information about these dependencies to relevant host(s); initiates deadlock checks
SPU Lock Manager 308
  Controls concurrent access to data
  Interfaces with EventTask 36 before a query is executed and for each result set returned from a scan
  Provides support for arithmetic locking
SPU Recovery Manager 312
  Maintains a Journal to track transaction status on the SPU 22, using the Storage Manager API
  Performs transaction recovery when requested by SPU Transaction Manager
SPU Mirror Manager 314
  Mirror Sender receives copies of record updates from Storage Manager 320 and transmits these to the mirror for this SPU when an updating transaction commits
  Mirror Receiver receives record updates, buffers these in memory, and flushes out to disk through the Storage Manager when the Mirror Receiver buffer is full
  Transmits all data to a spare system during failover processing
Storage Manager 320
  Stores and manages information on disk in optimal fashion
  Has an API that supports storage and retrieval of tuple sets
  Supports error checking to insure that the data conforms to the indicated table and the indicated table "owns" the physical space to which the data is being written
  Supports creation and deletion of tables, views, and indices
  Handles record inserts and deletes
  Supports ETL and mass loading of existing user data
  Provides storage support for commit/rollback
  Provides support for Precise Indexes
  Provides mirroring support for failover
  Optimizes sort operations and utilizes smart hash algorithm for data distribution/striping
  Provides support for compression and smart storage optimization
  Controls disk I/O
SPU Resource Scheduler 322
  Schedules jobs to run on the PSDP 28; communicates with SPU/PSDP Scheduler 324 to queue up PSDP requests to retrieve required data
  Optimizes the queue to keep the PSDP/disk as busy as possible, with requests from multiple queries intermixed in the queue based on disk characteristics and location of data on the disk
  Takes into account the needs of any data loading for new tables being created and transformed to internal data format (i.e., to optimize the loading process)
  Supports heuristic-based scheduling, ensuring that jobs are scheduled on a priority basis, but also ensuring that all jobs do get serviced (e.g., raising a job in priority if it has not been run in a certain interval of time)
  Supports synchronous/piggy-backed scans, combining similar requests to optimize PSDP processing
  Manages memory buffers/memory allocation on SPU; allocates memory to Execution Plans based on expected needs and hints received from Plan Optimizer
SPU Paging (if required)

PSDP Prep 330
  Defines the instructions that will be given to the PSDP 28 in order to process a request (instructions tell the PSDP 28 what to do with each field being read from the disk)
  Identifies what filtering, transformation, projection, and aggregation operations are to by run by the PSDP 28
EventTask 310
  Executes the portion of the Execution Plan that could not be handled by the PSDP but that does not have to be handled at the Host level
  Handles sorts, joins, transformations, and aggregations that could not be done as data stream through the PSDP 28
  Maintains a memory buffer of result set records and returns these to Host through the Comm Layer when buffer filled, job completed, or at Host request
SPU Diags 332
  Runs diagnostics on SPU as required/requested
SPU Boot/Init 334
  Executes image burned into flash memory at boot time to bootstrap the SPU, run diagnostics, register the SPU with the primary Host server, and download new image from Host to run
  Loads and transfers control to the image downloaded from the primary Host server to load the SPU application code, the operating system, the network stack, and disk driver code
Backup/Recovery 336
  Supports SPU side of Backup/Recovery process
  Interfaces with Transaction Manager and SPU Storage Manager
DBA Lite 338
  Provides automatic and dynamic disk and Storage Manager support
  Supports dynamic index creation, defragging, index garbage collection, timers, agents
SPU/PSDP Scheduler 324
  Schedules jobs to run on the PSDP; queues up PSDP requests to retrieve required data B. SQL Query Based Comparison Operation on Sequence Data The query language operates on sequence data that has been stored or represented by relations (also known as tables). Each relation contains some number of tuples (also known as rows or records). Each tuple consists of data values organized in columns (also known as fields).

As now understood from the above architecture discussion, in a preferred embodiment the database is a parallel database whereby a given user-supplied SQL query may be simultaneously executed on some or all of multiple SPUs 22. Specifically, the SQL is broken into component pieces (called 'snippets') that the SPUs 22 execute on their portion of the total data system (called 'clataslice').

Since a query often involves table joins, sorts, and aggregations—these queries often require that data be sent to a given SPU 22 that does not already have a copy of the data. In some cases, the 'new' data is sent to every SPU 22 (called a 'broadcast'). In other cases, SPUs may selectively receive different datasets (called a 'distribute'). This broadcasting and distributing is handled by query snippets, along with the specific joins, sorts, aggregations and other database query operations.

In the Preferred Implementation (PIM) of the present invention, the subject or so-called "haystack" sequences of amino acids are stored as a sequence of bytes where each amino acid molecule is represented by a single byte containing the amino acid encoding number. Since there are only about 20 different amino acid types, the PIM can also store amino acid sequences in fewer bits. One such implementation uses between 5 and 7 bits per molecule. Another implementation allows for a 4-bit molecule with the balance of the values using "escaped" encodings.

Since nucleotide sequences are described by only four different molecule types, haystack sequences for nucleotides are stored using two binary bits per molecule. For nucleotide sequences, there are also optional additional per-sequence lists to describe nucleotide ambiguities and case-masking. An ambiguity list entry is an index into the sequence that specifies that at the indexed location the value is not one of the common A/C/G/T (0/1/2/3) values—instead it is another value described by a byte value in the index. A case-masking list entry is likewise an index that describes an area of different significance. The case-masking index may include either a bitmask or a start-span list.

PIM query processing is a pipeline with minimal materialization steps. As with other joins, the result set is not materialized into tuples unless the next step of the pipeline is an explicit materializing step, such as a sort—in which case, the materialization is handled by the general sorting logic as is the case with other joins in the PIM.

BLAST Join Syntax

Blast joins are part of the database system using two allowed syntax conventions in the PIM. In the "SQL-92 Full Syntax" implementation discussed below, the join elements are presented in an un-ambiguous manner. The "Shorthand" syntax is simpler but includes an ambiguity described below.

SQL-92 Full Syntax

As was described earlier, a blast alignment is treated as a new type of join. Specifically, we are aligning some number of small query or so-called "needle" records against a typically larger number of "haystack" records. Each record may contain any number of fields, but at least one field from each record must be an amino-acid or nucleotide sequence. The needles table is also allowed to be a single literal string.

In addition, we define a "controls" table, which is typically just presented in the query as a single literal string. This string (or table of strings) is the "command line switches" to the blast operation in "NCBI blastall" format.

The syntax is an extension of the SQL92 generalized join syntax:
SQL92: SELECT <cols> FROM <t1> <jointype> <t2> ON <join-condition>
The blast join syntax, where the controls is a literal string, is thus:
SELECT <cols>
FROM <haystack> [ALIGN <needles>] [WITH <controls>]
ON BLASTX(<haystack.seq>,<needles.seq>,<controls.args>)
  where BLASTX is any of "blastn", "blastp", "blastx", "tblastn", "tblastx",
  where haystack, needles and controls are tables/relations including possible sub-select results,
  where the data types of the BLASTX ".seq" arguments are either protein, nucleotide or convertible text based on the standard BLASTX type, and
  where the controls.args is varchar.
Thus a simple literal protein blast looks like:
SELECT <cols> FROM haystack ON BLASTP(haystack.seq, 'ZZAADEDAAM', '-e.001')
The controls parameter may be a table so that it is possible to perform cross-product analysis varying controlling factors such as gap open and extend costs.

Note too that this can be combined into multiple blasts in the same query in a non-ambiguous manner:
SELECT match1.pseudo_fld1, match2.pseudo_fld2, haystack1.field1, haystack2.field1, . . . FROM haystack1
ALIGN needles WITH controls ON BLASTX (haystack1.gene, needles.seq, controls.arg) as match1, haystack2
ALIGN needles WITH controls
ON BLASTX(haystack2.gene, needles.seq, controls.arg) as match2,
. . .
WHERE
. . .
Here in this form of syntax we can clearly state where the pseudo fields are coming from, whether match1 or match2 by able to tag them with the aliases.

PIM Alternate "Shorthand" Syntax

The shorthand syntax is consistent with how most database equi-joins are described.
SELECT <cols>
FROM <haystack> [, <needles> [,<controls>]
WHERE BLASTX(<haystack.seq>,<needles.seq>,<controls.args>)
In this syntax, the BLAST function is considered a boolean psuedo-function. In the PIM, the query parser detects the usage of this call (which is only used in Blast joins), identifies the haystack, needle and controls tables, and produces the associated join parse tree. Note that the tables do not need to be presented in haystack/needle/controls order in the FROM clause—the table identification is handled by evaluating the arguments to the BLAST function.

As with other joins, this can be combined with other join qualifications such as:
SELECT <cols>
FROM haystack,needles,clinical
WHERE BLASTN(haystack.seq, needles.seq, "0.0001")
  AND clinical.info=haystack.info
Multiple joins in the shorthand form lead to an ambiguity. Consider the following example:
SELECT pseudo_fld1, pseudoild2,haystack1.field1, haystack2.field1, . . .
FROM haystack], haystack2, needles, controls, . . .
WHERE
  BLASTX(haystack1.gene, needles.seq, controls.arg)
  AND
  BLASTX(haystack2.gene, needles.seq, controls.arg)
  AND
In the above syntax it is not possible to un-ambiguously to state where the pseudo_fld1, pseudo_fld2 fields are coming from because both BLASTX functions produce these fields. In other words, the SQL parser will reject such a statement, requiring the implementer to specify a non-ambiguous form, i.e., depending upon whether the fields come from the haystack1 blast join or the haystack2 blast join.

BLAST Join SQL Semantic

The BLAST algorithm is integrated into the database in such a manner that it is abstracted as a relation "join" operation.

The subject sequence list (also called the 'haystack') is joined against the query sequence list (also called the 'needles').

The subject sequence is a field in a SQL tuple (called the 'haystack' row in the PIM). In addition to the sequence material, the haystack tuples may include additional fields that describe the origin of the sequence or other attributes of the sequence and any other information related to the sequence.

Similarly, the query sequence is a field in the needle tuple. The additional fields in the needle tuples may (or may not) be similar to the additional fields included with the subject sequence to form the haystack tuple.

Also permitted is the degenerate case of a single literal representation of a query and/or subject sequence. In the underlying implementation, this is equivalent to a single-row table.

In the PIM, an additional relation (called 'controls') is also provided to allow the user to specify the BLAST control characteristics. In the PIM, this control string or table is based on the command line conventions of the standard, standalone BLAST program, "blastall".

The SQL syntax and semantic allows for each of the query sequences to be compared to each of the subject sequences. This is performed for each of the controls.

Consistent with how the PIM handles SQL relations in general, during the SQL query all of these relations may originate from the disk, the communications fabric, RAM memory storage, or other memory devices or they may be assembled from prior parts of the SQL query.

If obtained from the disk or other memory storage, they may have been placed there from previous SQL queries or other non-SQL loading/caching tools.

The SQL join of the haystack with the needles (for each controls) results in zero or more result tuples. Unlike all other SQL joins, the number of tuples in the result relation (for each controls) is permitted to be larger than the multiplicative product of the number of tuples in the haystack by the number of tuples in the needles table, to accommodate multiple points of alignment between each combination of needle and haystack Result Relation of the Blast Join The result set of the Blast join is a tuple for each "high scoring pair" in Blast (XML) parlance. A "local alignment" or "hit" (XML) includes one or more of these HSPs.

The exact definition of HSP and Blast's XML-format output are available at http://www.ncbi.nih.gov.

Thus, the haystack/needle tuple-pairs for which there are zero local alignments are not present in the result set at all.

Each result tuple conceptually consists of all of the fields of the needle and haystack tuples. In usage, most queries are expected to request a "projected" subset of these fields. In the PIM, the non-requested fields are not materialized, saving processing time and storage costs.

Each result tuple also contains a number of "psuedo-fields" that detail the aspects of the local alignment. For local alignments that combine to form a "gapped alignment", each of the tuple's psuedo fields also include the information about the gapped alignment.

The exact list of psuedo fields varies based on the type of alignment performed, but as a minimum, include the starting positions and match-spans in the query sequence and subject sequence. Additional psuedo fields common to all Blast joins include a statistical value (the "expect" value) describing the likelihood of random matches and a "score" value that may be used to compare this alignment against others.

Additional psuedo fields are supplied which contain information directly derived from other fields. For example, the sub-sequence of the haystack and needle that the match occurred on is offered as a psudo-field in the PIM.

BLAST Join Implementation Summary

A Blast join is typically part of potentially much larger query execution plan. A query execution plan is typically represented as a "tree" or "sequence" of plan execution nodes, where each node relates to a step in the query processing. Some common node types are "scan", "aggregate" and "join". The join types are further divided into "hash", "nested-loop", "merge", "exists" and others. Each of join types may be further sub-grouped into "inner", "outer", "disk-based" and so on.

In the PIM, the execution plan is created by the SQL Parser and Optimizing Planner. The parser converts the SQL language text into a plan tree form. The original query may have any number of joins and restrictive clauses. This tree is then analyzed on a "cost-basis" to produce an optimal execution plan. The optimal plan is the one that runs fastest and/or uses the least amount of memory or disk space as defined by the predefined costs associated with time and resources.

In the PIM execution plan, there is a new join node type, "BlastJoin". This node type operates on a total of four relations. Of the four, three have been pre-materialized by previous steps in the execution plan. The pre-materialized tables are referred to as the "inner table", the "controls table", and the "haystack stats".

The fourth table is referred to as the "outer" or "streaming" table and is, in the PIM, conceptually considered the input to the join on a per-tuple basis. Thus, the PIM's execution plan's nodes can be considered as a set of processes, each of which pipeline tuples to the next node. In fact, the outer table is often materialized by a previous node and the pipeline is really just a do-loop that steps through each row and provides it to the join node.

Depending on how the optimizing planner has organized the execution plan, the inner table may be either the haystack or the needles table. Based on the cost-values in the PIM, if the needles and supporting Blast runtime state are known to be able to fit in a small amount of RAM memory, the inner table may be the needles table and the haystack is the outer table. Conversely, if the haystack fits in a small amount of RAM, it may become the inner table. If neither table fits in memory, a disk-based algorithm is used and the inner table is usually the haystack.

The ultimate choice which of the haystack or needles is the inner or outer table is the responsibility of the optimizing planner based on cost estimates.

The "haystack stats" table is a small relation that in the PIM, contains the size of the haystack relation in rows and the sum of the sizes (in molecules) of each of the subject sequences.

Auxiliary Output Tables

The PIM allows the sequence analysis algorithm to produce additional tables separate from the join result set. These tables are "side-effect" tables and are invisible to the query statement that contains the Blast join, but are visible to subsequent SQL statements.

For Blast joins, the PIM produces a histogram table and summary table.

These auxiliary tables are only created if requested as part of the PIM controls record. The control string specifies the names of the tables and their scope (i.e. whether they are to be transaction-scoped, session-scoped, permanent tables, etc).

Parallel Techniques

The PIM uses a "host" processor to initiate and control overall query execution and combine and then send the result set to the client program. For queries that operate against a pre-existing disk-based table, the host processor is also used to load the initial haystack table, typically from files created by other programs. For queries that operate against a relation that is the result set of a previous step in the query script, the haystack may be present on the SPUs as a result of host-based distribute or the SPUs may distribute the data amongst themselves.

In the PIM, the haystack table is distributed in an approximately even manner across all of the SPU disks in the system. The table is distributed as whole records—all of the fields associated with a given record are present together on the same SPU.

The distribution strategy can be any of a number of algorithms, such as "round-robin", "hashed", "sized" or "custom". In a round-robin distribution, each of the first N records are sent to each of the N SPUs. The next N records are likewise sent to the N SPUs. Thus, the formula for where a given record goes is roughly "destinationSPU=recNum % numSPUs", where the "%" is the modulo operator. In a hashed distribution, some number of the haystack fields in each record are combined using a hashing algorithm such as CRC (cyclic redundancy check) to choose the destination SPU. In a sized algorithm, the distribution of the records is adjusted to allow for each SPU to receive a number of records bytes roughly equal to the number of bytes on each other SPU. In a custom algorithm, the algorithm may use any number of internal measures and choices to decide where a haystack record is sent.

The invention also allows for groups of records to be duplicated on some or all of the SPUs, even to the extent that each SPU can contain the full haystack. In this scenario, the query is executed in a slightly different manner—instead of the each SPU using the full needle set, each SPU can use a subset. In the case where each SPU contains the full haystack, each SPU would use a unique needle set.

In the PIM, the needle table is fully duplicated on all of the SPUs. For most Blast joins, this is done by the host processor broadcasting the records to all SPUs whereupon they each materialize the full needle record set.

Note that some sequence analysis programs are needle/haystack symmetric. The database's choice about which table is broadcasted versus distributed is allowed to be decided at query time based on a user directive or the database's own internal optimal query-planning analysis.

An Example Schema for the Database

This example is based on a single haystack/needles table. Thus, the blast join is actually a self-join. We think this is consistent with many of the queries used when comparing sequences from an organism already in the database against many other organisms in the database.

To take advantage of the non-redundant FASTA (the standard file format for describing biological sequences) file formats, we split the sequence data from the information data linked by a unique primary key.

The following is the schema for our protein table pair:

```
create table prot_seq (                      \
    s_uid int8 primary key,                  \
    s_seq protein not null) distribute on (s_uid);
create table prot_info (                     \
    i_uid int8 references prot_seq(s_uid),   \
    i_fasta varchar(100),                    \
    i_initial boolean,                       \
    i_name varchar(100),                     \
    i_description varchar(300)) distribute on (i_uid);
```

In the tables above (and views below), the "i_fasta" field is the filename of the original FASTA file and the name and description fields are from the sequence header lines.

```
create view vpemp as select * from prot_info, prot_seq where \
    i_fasta = 'prot_emp' and i_uid=s_uid and i_initial=true;
create view vpgrp as select s_seq q_seq, i_name q_name \
    from prot_info, prot_seq \
    where i_fasta = 'prot_grp' and i_uid=s_uid and i_initial=true;
```

Since the alias syntax for self joins is hard to read, we create two views—one view being the needles (called vpgrp here) and the other being the haystack (called vpemp here). Then the actual blast query is against the views. The I_initial field is the first definition of the sequence in the FASTA file.

Thus, a query looks like:

```
SELECT i_name, score, q_name, ctrl \
FROM vpemp ALIGN vpgrp WITH ctrlspx ON \
    blastp(vpemp.s_seq, vpgrp.q_seq, ctrl) \
order by i_name, q_name, score
```

Naturally, the user's schema and approach don't have to look this way—even if they use a single-table approach, the aliased subselects can be in the FROM and ALIGN clauses above. It likewise goes almost without saying that the haystack and needles can be derived from any prior joins, restricts and the results of the blast can be joined and aggregated like any other intermediate result set.

Details of a Blast Join Execution Plan

This section uses the following example SQL script for the discussion:

```
-- List the contents of each of the haystack, needles, controls tables:
-- Haystack
select * from pemp;
-- Needles
select * from pgrp;
-- Controls
select * from ctrlspx;
-- Perform a simple Blast join of all needles into the
haystack, returning
-- the needle-id and haystack-id from the outer and inner tables and
-- also returning several psuedo-fields, including an expression on one
-- of them.
SELECT q_name, i_name, hit_num ,hsp_num ,hsp_bit_score ,hsp_score
    ,hsp_evalue ,hsp_query_from ,hsp_query_to ,hsp_hit_from
    ,hsp_hit_to ,hsp_qseq ,hsp_hseq ,hsp_midline
,length(hsp_midline)
FROM pemp
SEARCH pgrp
WITH ctrlspx
ON blastp(pemp.s_seq, pgrp.q_seq, ctrl);
```

The output of this script against a sample set of tables is as follows:

```
    i_uid    I i_fasta I i_initial I i_name I      i description           s_uid
                                              s_seg
---------------------------------------------------------------
---------------------------------------------------
4563965701203919673 I prot_emp ₁ ᵣ   I emp1 I One match against grp        14563065701203919673
I Z2MATCHIT
4563865781203919674 I prot_emp ¹ʳ    I emp2 I No matches against grp      I 4563065791203919674
I DEADMEAT
4563665781203919675 I prot_emp       I emp3 I Member of multi-record match against grp 14563865781203919675
I AAACCCTTT
4563065781203919676 I prot_emp I t   I emp4 I Member of multi-record match against grp 14563865781203919676
I AAACCUTTIIAAACCCTTT
4563865781203919677 I prot_emp I t   I emp5 I Member of multi-record match against grp 14563865701203919677
I AAACCCTTTIIAAACCCTITIIAAACCCTTTIIAAACCCTTTIIAAACCCGTTIIAAACCCTTTIIAAACCCTGTIIAAACCCTTTIIAAACCCTTTII
(5 rows)
    q_seq         I q_name
 Z2MATCHIT        I grp1
 _MEATDEAD        I grp2
 AAACCCTTT        I grp3
 IIAAACCCTTT      I grp4
(4 rows)
 ctrl
-------
 -e.0001
(1 row)
```

```
q_name I i_name I hit_num
                        I hsp_num I hsp_bit_scOre   I            hsp_score I        hsp_evalue I
                                                                                    hsp_qUery_from I
hsp_query_to I          I hsp_hit_to     I        hsp_ciseq    I hsp_hseg  I
hsp_hit_from                                       hsp_midline I        length --------
             4 -------
     4 ----------
 grp3    I emp5       1   I      1        125,409009379501
                                                          I           54  17.2722072831518e-05
 9 I        09         97I AAACCCTTT      I AAACCCTTT   I   AAACCCTTT  I   9
 grp3    I emp5       1   I      2        I25.409009379501
                                                        I             54  17.2722972031510e-05
 9 I        78         86 I AAACCCTTT     I AAACCCTTT       AAACCCTTT  1   9
 grp3    I emp5       1   I      3        I25.409009379581
                                                        I             54  17.2722672831518e-05
 9 I        56         64 I AAACCCTTT     I AAACCCTTT       AAACCCTTT  I   9
 grp3    I emp5       1   I      4        I25.409009379501
                                                        I             54  17.2722072031516e-05
 9 I        34         42 I AAACCCTTT     I AAACCCTTT       AAACCCTTT  I   9
 grp3    I emp5       1   I      5        I25.409009379581
                                                        I             54  1 7.2722872931510e-05
 9 I        23         31 I AAACCCTTT     I AAACCCTTT       AAACCCTTT  I   9
 grp3    I emp5       1   I      6        I25.40900093795⁸⁾
                                                        I             54  I 7.27228728315113e-05
 9 I        12         20 I AAACCCTTT     I AAACCCTTT       AAACCCTTT  I   9
 grp3    I emp5       1   I      7        I25.409009379581
                                                        I             54  I 7.2722872831516e-05  I
 9 I         1          9 I AAACCCTTT     I AAACCCTTT       AAACCCTTT  I   9
 grp3    I emp4       2   I      1        I25.409009379501
                                                        I             54  17.2722872031510e-05  I
```

-continued

| | | | | | | | | | |
|---|---|---|---|---|---|---|---|---|---|
| 9 I | | 12 | 20 I AAACCCTTT | I AAACCCTTT | AAACCCTTT | I | 9 | | |
| grp3 | I emp4 | 2 I | 2 | I 25.409009379581 I | | 54 | I 7.2722872931518e-05 I | | |
| 9 I | | 1 | 9 I AAACCCTTT | I AAACCCTTT | AAACCCTTT | I | 9 | | |
| grp3 | I emp3 | 3 I | 1 | I 25.409009379581 I | | 54 | I 7.27221372831516e-05 I | | |
| 9 I | | 1 | 9 I AAACCCTTT | I AAACCCTTT | AAACCCTTT | I | 9 | | |
| grp4 | I emp5 | 1 I | 1 | I 28.49060598692 I | | 62 | I 8.5904915207764e-06 I | | |
| 11 I | | 87 | I 97 I IIAAACCCTTT | IIIAAACCCTTT | IIAAACCCTTT | I | 11 | | |
| grp4 | I emp5 | 1 I | 2 | I 20.49060598692 I | | 62 | I 8.5904915207764e-06 I | | |
| 11 I | | 76 | I 86 I IIAAACCCTTT | I11AAACCCTTT | IIAAACCCTTT | I | 11 | | |
| grp4 | I emp5 | 1 I | 3 | I 28.49060598692 I | | 62 | I 8.5904915207764e-06 I | | |
| 11 I | | 54 | I 64 IIIAAACCCTTT | I IIAAACCCTTT | IIAAACCCTTT | I | 11 | | |
| grp4 | I emp5 | 1 I | 4 | I 28.49060598692 I | | 62 | I 8.5904915207764e-06 I | | |
| 11 I | | 32 | I 42 I IIAAACCCTTT IIAAACCCTTT | | I | IIAAACCCTTT | I 11 | | |
| grp4 | I emp5 | 1 I | 5 | I 28.49060598692 I | | 62 | I 6.5904915207764e-06 I | | |
| 11 I | | 21 | I 31 I IIAAACCCTTT IIAAACCCTTT | | I | IIAAACCCTTT | I 11 | | |
| grp4 | I emp5 | 1 I | 6 | I 28.49060598692 I | | 62 | I 9.5904915207764e-06 I | | |
| 11 I | | 10 | I 20 IIIAAACCCTTT | I IIAAACCCTTT | 11AAACCCTTT | I | 11 | | |
| grp4 | I emp5 | 1 I | 7 | I 25.794208955498 I | | 55 | I 5.5681945406694e-05 | I | 1 |
| 11 I | | 65 | I 75 IIIAAACCCTTT | I IIAAACCCTGT | IIAAACCCT T | I | 11 | | |
| grp4 | I cops | 1 I | 8 | I 25.794200955490 I | | 55 | I 5.5681945406694e-05 I | 1 | |
| 11 I | | 43 | I 53 IIIAAACCCTTT | I IIAAACCCGTT | IIAAACCC TT | I | 11 | | |
| grp4 | I emp5 | 1 I | 9 | I 25.409009379501 I | | 54 | I 7.2722872931516e-05 I | | 3 |
| 11 I | | 1 | I 9 I AAACCCTTT | I AAACCCTTT | AAACCCTTT | I | 9 | | |
| grp4 | I emp4 | 2 I | 1 | I 25.49060598692 I | | 62 | I 8.5904915207764e-06 I | | |
| 11 I | | 10 | I 20 IIIAAACCCTTT | I IIAAACCCTTT | IIAAACCCTTT | I | 11 | | |
| grp4 | I emp4 | 2 I | 2 | I 25.409009379581 I | | 54 | I 7.2722872831516e-05 | f | 3 |
| 11 I | | 1 | I 9 I AAACCCTTT | I AAACCCTTT | AAACCCTTT | I | 9 | | |
| grp4 | I emp3 | 3 I | 1 | I 25.409009379581 I | | 54 | I 7.2722872831516e-05 | I | 3 |
| 11 I | | 1 I | 9 I AAACCCTTT | I AAACCCTTT | AAACCCTTT | I | 9 | | |

(22 rows)

Figure 5:
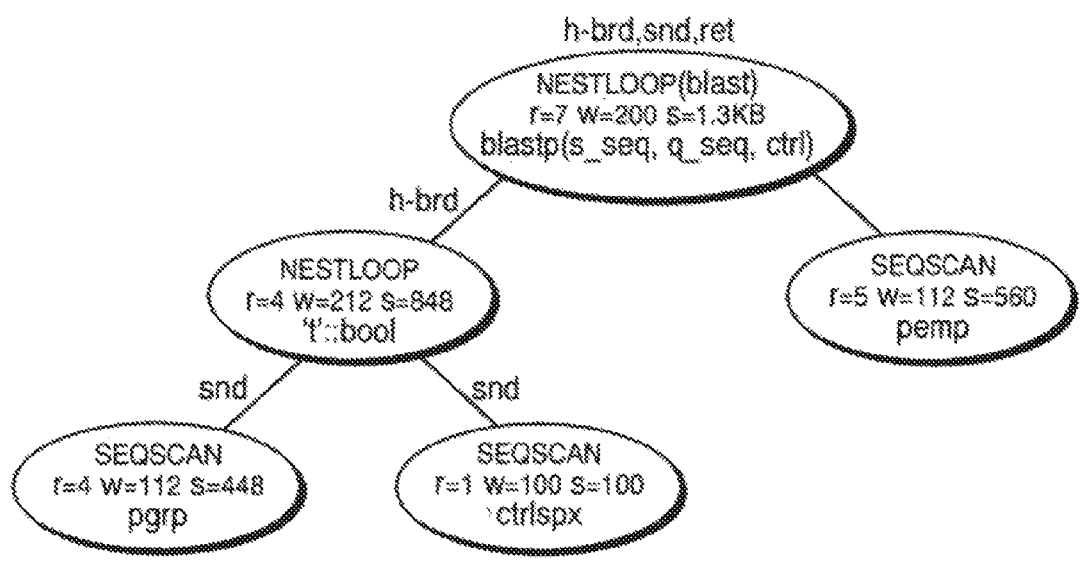
FIG. 5 is a flow diagram of an example plan for carrying out a sequence comparison formulated as query language statements.

A tree-form of the Blast Join execution plan is shown in FIG. 5.

Reading from the bottom to the top, this plan specifies that the "ctrlspx" table is to be scanned into memory in the host processor 12 as an inner table. Then the "pgrp" needles table is scanned and the records are cross-product joined to the inner table. The resultant records are broadcasted to all of the SPUs 22. There, they are joined against a scanned-in "pemp" table to produce the Blast result set. The r/w/s in this notation are an indication of some of the sizing factors used by the optimizing query planner to choose the best execution plan.

The flattened, detailed execution plan is significantly more complex. It begins with a statistics scan of the haystack ("pemp"). This is done because the NCBI Blast algorithm requires the number of sequences and the byte-size of the haystack table as input. These values can be included as part of "ctrlspx" table options, in which case the statistics scan is not present.

An example plan appears several paragraphs below in the text. In this plan description, the numeric column (of the form N[XX]) designates the snippet number and the per-snippet execution step. A snippet is a unit of execution plan compilation and execution.

Each snippet runs on either the host 12 ("dbs") or the SPUs 22 ("spu") as designated by the second column. All snippets are compiled on the host processor. If the snippet is to execute on the SPU, it is broadcast to the SPU by the host.

In reading the following plan, note that the "large" numbers are table-ids. Those table-ids that are greater than 1,000,000,000 are in-memory tables. If an in-memory table exceeds the amount of available memory, it is spilled to the disk in a "paging" manner.

Most of the nodes below are self-describing with a knowledge of standard relational database technology. However, the "ReturnNode" means this locus is returning records to the calling locus—in an SPU, the records are returned to the host. The Table SizeNode is a runtime statistics reporting mechanism that allows the detailed execution engine to choose between memory-based or disk-based algorithms for the subsequent joins.

The records that are implicitly exiting join nodes are the combined outer‖inner fields. The records exiting Aggregate nodes are the combined input‖grouping‖aggregated fields.

The Blast join node is part of the snippet #5, denoted below beginning with "5[00]".

Here is the example plan:

```
 1[00]: spu ScanNode table "pemp" 200653 memoryMode=no flags=0x202
        -- Cost=0.0..0.1 Rows=5 Width=112 Size=560 {(i_uid)}
 1[01]: spu RestrictNode (NULL)
 1[02]: spu ProjectNode, 2 cols
        3:i_name 6:s _seq
        -- 0:i_name 1:s_seq
 1[03]: spu SaveTempNode
        as temptable 1000000503 transient=0 append=0
 1[04]: spu TableSizeNode table 1000000503
 1[05]: spu ReturnNode
501[00]: dbs TableSizeNode table 1000000503
 2[00]: spu ScanNode table 1000000503 memoryMode=yes flags=0x4
 2[01]: spu RestrictNode (NULL)
 2[02]: spu ProjectNode, 1 cols
        1:
 2[03]: spu AggregateNode 0 group fields, 2 aggrs method 0
        COUNT srcCol=0 srcType=0 dstType=20 distinct=0 tb1=0
        LEN srcCol=0 srcType=0 dstType=20 distinct=0 tb1=0
 2[04]: spu ProjectNode, 2 cols
        1: 2:
 2[05]: spu ReturnNode
502[00]: dbs AggregateNode 0 group fields, 2 aggrs method 0
        SUM srcCol=0 srcType=20 dstType=20 distinct=0 tb1=0
        SUM srcCol=1 srcType=20 dstType=20 distinct=0 tb1=0
502[01]: dbs ProjectNode, 2 cols
        2: 3:
502[02]: dbs DownloadTableNode broadcast into link 1000000504
 3[00]: spu ScanNode table "ctrlspx" 200689 memoryMode=no flags=0x0
        -- Cost=0.0..0.0 Rows=1 Width=100 Size=100
 3[01]: spu RestrictNode (NULL)
 3[02]: spu ProjectNode, 1 cols
        0:ctrl
        -- 0:ctrl
 3[03]: spu ReturnNode
503[00]: dbs SaveTempNode
        as temptable 1000000505 transient=0 append-0
503[01]: dbs TableSizeNode table 1000000505
 4[00]: spu ScanNode table "pgrp" 200679 memoryMode=no flags=0x203
        -- Cost-0.0..0.0 Rows=4 Width=112 Size=448 ((q_name))
 4[01]: spu RestrictNode (NULL)
 4[02]: spu ProjectNode, 2 cols
        1:q_name 0:q_seq
        -- 0:q_name 1:q_seq
 4[03]: spu ReturnNode
504[00]: dbs CrossProductNode table 1000000505
        -- 't'::bool
        -- Cost=0.1..0.9 Rows=4 Width=212 Size=848
504[01]: dbs ProjectNode, 3 cols
        2:? 0:? 1:?
        -- 0:ctrlspx.ctrl 1:pgrp.q_name 2:pgrp q_seq
504[02]: dbs DropTableNode 1000000505
504[03]: dbs DownloadTableNode broadcast into link 1000000506
 5[00]: spu ScanNode table 1000000506 memoryMode=yes flags=0x4
 5[01]: spu ProjectNode, 3 cols
        0: 1: 2:
 5[02]: spu BlastJoinNode
        table 1000000503 tblField=1 joinField=2 ctrlField=0 blastType=2 rowCntId=1000000504
        -- blastp(pemp.s_seq, pgrp.q_seq, ctrlspx.ctrl)
        -- Cost=5.0..30008.1 Rows=7 Width=200 Size=1.3KB {(pemp.i_uid)}
 5[03]: spu ProjectNode, 15 cols
        1:g_name 3:i_name -32:hit_num -37:hsp_num -38:hsp_bit_score -
39:hsp_score -40:hsp_evalue -41:hsp_query_from -42:hsp_query_to -43:hsp_hit_from
44:hsp_hit_to -54:hsp_qseq -55:hsp_hseq -56:hsp_midline 14:length(blastcol(-56))
```

```
5[04]: spu DropTableNode 1000000503
5[05]: spu DropTableNode 1000000506
5[06]: spu DropTableNode 1000000504
5[07]: spu ReturnNode
505[00]: dbs ReturnNode
End Execution Plan
```

In the context of this invention, the most relevant node in the plan above is the BlastJoinNode. It describes the implementation of the Blast join as operating on the needles outer table, 1000000506, (actually the cross-product of "pgrp" and "ctrls") and the joining of that against the inner haystack (1000000503 derived from "pemp"). The join is performed on the inner tables field #1 against the outer table's field #2. The control string is part of the outer table, at field #0. This join is a blastType=2 which denotes a blastp operation. For the haystack statistics, it refers to the previously broadcast single-record stats table, 1000000504.

The projection that follows the join node defines which fields of the combined tuplesets are to be passed onto the next step of the plan. In this case, the first two fields are from the outer and inner tables and the subsequent (field numbers <0) are blast-specific psuedo-fields.

Detailed Implementation of the Blast Join

The following "C++ code" is the instantiation of the snippet #5 of the execution plan listed above.

The PIM uses a model of fully compiled queries as described in a co-pending U.S. Patent Application entitled "Optimized SQL Code Generator II,", Ser. No. 60/485,638 filed Jul. 8, 2003, the entire contents of which is hereby incorporated by reference.

In this system, the query plans are realized directly as a set of query-specific C++ statements that are compiled and dynamically bound into the execution of the database, all at query time. This invention also works with more traditional "interpretive" query engines.

In the following code, most data types and variables include the snippet node number in their names (the [XX] in the plan above). Therefore:

TScan0 is structure definition for the records of the "5[00]" ScanNode.

Scan0 is the record pointer to the current record of the Scan0 loop.

tScan0 is a pointer to the table object that describes the nature of the fields and their constraints, plus the current state of this table instance, such as a ptr to the memory areas that contain this table's in-memory records. The TScan0 structure is essentially derived from this structure.

The blastAway( ) call implements the record-pair (1needle, 1haystack) join. It also loads the tBlastOut2 table the HSP result records.

In the code below, each varying size field is denoted in the records structure of type vlen_t fielded[0]. This is a placeholder for readability convenience. The actual field is obtained by calling GetVarFieldPtr( ).

The coalesce( ) function is to convert a disk/network representation of a sequence to a single memory allocation. Likewise the coalesceAll( ) performs the same action for all of the records in a memory-materialized relation.

The FIRST_BLOCK and LOOP_RECS_VARIABLE macros are used to loop thru records grouped in blocks. The LOOP_RECS_VARIABLE sets its first argument, which is then used in the contained code.

The VERIFY_FSPACE macros test a block to see whether it has sufficient room to fit the requested size. If it does not, the block is handed to the named function (the last argument) and a new block is allocated, setting the fourth argument.

The sliceAndDice( ) function takes in an in-memory coalesced sequence and parcels it into one or more blocks. If it doesn't all fit in the current block, sliceAndDice calls the function specified by the eighth argument to process the block and then slideAndDice( ) allocates a new block buffer to its sixth argument.

The UPDATE_WRITE_ADDR makes the block buffer's internal pointers aware of the material that had been copied into it.

The returnNewBlock( ) and returnNewBlockFunc( ) are routines that arc used in the SPU to send the contents of the current block buffer to the host.

```
#include "geninl.h"
/********** Prefix **********/
struct TScan0 (
            uint16 size;
            uint8 nulls[1];
            uint8 pad1[1];
vlen_t f0[0];vlen_t f1[0];vlen_t f2[0];
);
struct TTemp2 (
            uint16 size;
            uint8 nulls[1];
            uint8 pad1[1];
vlen_t f0[0];vlen_t f1[0];
);
struct TBlastOut2 (
            uint16 size;
            uint8 pad1[2];
double f9;double f10;double f28;double f29;
double f30;double f50;double f51;double f52;double f53;
int f6;int f11;int f12;int f13;int f14;int f18;int f21;int f22;int f26;int f27;int
f31;int f32;int f33;
```

```
int f34;int f35;int f36;int f37;int f38;int f39;int f40;int f41;int f42;int f43;int
f47;int f48;int f49;int f55;
vlen_t f0[0];vlen_t f1[0];
vlen_t f2[0];vlen_t f3[0];vlen_t f4[0];vlen_t f5[0];vlen_t f8[0];vlen_t f19[0];vlen_t
f20[0];
vlen_t f23[0];vlen_t f24[0];vlen_t f25[0];vlen_t f54[0];vlen_t f7101;vlen_t
f15[0];vlen_t f16[0];
vlen_t f17[0];vlen_t f44[0];vlen_t f45[0];vlen_t f46[0];
);
struct TReturn7
              uint16 size;
              uint8 nulls[2];
  double f4;double f5;double f6;
  int f2;int f3;int f7;int f8;int f9;int f10;int f14;
  vlen_t f0[0];vlen_t f1[0];vlen_t f11(0];vlen_t f12[0];vlen_t f13[0];
/********* Code **********/
void GenPlan5(CPlan *plan, char *bufStarts,char *bufEnds, bool lastCall) {
      int bufSize = bufEnds - bufStarts;
  TScanNode *node0 = (TScanNode*)plan->m_nodeArray[0];
           TScan0 *Scan0 = BADPTR(TScan0*);
           CTable *tScan0 = plan->m_nodeArray[0]->m_result;
  char *nullsScan0P = BADPTR(char *);
  TProjectNode *node1 = (TProjectNode*)plan->mnodeArray[1];
  TBlastJoinNode *node2 = (TBlastJoinNode*)plan->m_nodeArray[2];
  if ( !(node2->m_tempTb1->m_blobsCoalesced) )
      node2->m_tempTb1->coalesceAll( );
  CTable *tTemp2 = node2->m_tempTb1;
  TTemp2 *Temp2 = BADPTR(TTemp2*);
  TTemp2 *Temp2Looper = BADPTR(TTemp2*);
  TMemblockInfo *block2 = NULL;
  if ( !node2->m_bLoaded)
      node2->LoadTempTable( );
  CTable *tBlastOut2 = node2->m QBlastOut;
  TBlastOut2 *Blast0ut2 = BADPTR(TBlastOut2*);
  TMemblockinfo *BlastOutBlock2 = NULL;
  // Created by Projection:
  // computed field 14
  int var13;
  bool var13Null = false;
  TProjectNode *node3 = (TProjectNode*)plan->m_nodeArray[3];
  TDropTableNode *node4 = (TDropTableNode*)plan->m_nodeArray[4];
  TDropTableNode *node5 = (TDropTableNode*)plan->m_nodeArray[5];
  TDropTableNode *node6 = (TDropTableNode*)plan->m_nodeArray[6];
  TReturnNode *node7 = (TReturnNode*)plan->m_nodeArray[7];
  TReturn7 *Return7 = BADPTR(TReturn7*);
  CTable *tReturn7 = node7->m_result;
  CRecordStore *recStore7 = tReturn7->m_recStore;
  TScan0 *nextScan0;
  for {Scan0 = (TScan0 *)bufStarts; (Scan0 < (TScan0 *)bufEnds); Scan0 = nextScan0}
           nextScan0 = (Tscan0*) ((char*)Scan0 + Scan0->size);
     if ( plan->m_interruptRequested ) GencAbortPlan(plan);
     if ( node0->m_blobs->coalesce((record_t**)&Scan0,NULL) )
        continue;
     uint32 innerRecNum2 =0;
     block2 = FIRST_BLOCK(tTemp2);
     LOOP_RECS_VARIABLE(Temp2Looper,TTemp2,block2)    |
        Temp2 = Temp2Looper;
        if ( plan->m_interruptRequested ) GencAbortPlan(plan);
        ( // Call external function to process data
             void *fields[3];
             // 0-haystack field, 1-needle field, 2-ctrls field
             fields[0] = GetVarFieldPtr((record_t*)Temp2,1,4);
             fields[1] = GetVarFieldPtr((record_t*)Scan0,2,4);
             fields[2] = Scan0->f0;
             // run the blast sequence into cache table
             node2->blastAway(fields,false,innerRecNum2++, (record_t*)Temp2);
        )
        Blast0utBlock2 = FIRST_BLOCK(tBlastOut2);
        LOOP_RECS_VARIABLE(BlastOut2,TBlastOut2,BlastOutBlock2) {
             Temp2 = (TTemp2*)Blast0ut2->f55;
             #define BlastOutRec BlastOut2
             (
                // Computed Columns
                var13
(*( int32**) ( ( (vlen_t*) (vlen_t*) (GetVarFieldPtr ( (record_t*)BlastOutRec,19,184 ) ) ) +1 ) ) ?
(* (* ( int32**) ( ( (vlen_t*) (vlen_t*) (GetVarFieldPtr ( ( record_t*)BlastOutRec,19,184 ) ) ) +1 ) )
) -
sizeof (Int32) : 0;
        // For ReturnNode:
             TMemblockInfo *block7 = recStore7->mlastBlock;
```

-continued

```
VERIFY_FSPACE(Return7,TReturn7,tReturn7,block7,2284,node7,returnNewBlock);
                block7->m_numRecords++;
                tReturn7->m_numRecords++;
                // materialize record into *Return7
                Return7->size = 56;
                char *Return7Pos = (char *)Return7 + 56;
                Return7->nulls[1] = 0;
                Return7->nulls[0] = 0;
                Return7->f4 = BlastOutRec->f28;
                Return7->f5 = BlastOutRec->f29;
                Return7->f6 = BlastOutRec->f30;
                Return7->f2 = BlastOutRec->f22;
                Return7->f3 = BlastOutRec->f27;
                Return7->f7 = BlastOutRec->f31;
                Return7->f8 = BlastOutRec->f32;
                Return7->f9 = BlastOutRec->f33;
                Return7->f10 = BlastOutRec->f34;
                uint16 lenScan0_p14;
                    Return7->f14 = var13;
                uint16 lenScan0_p0;
                    void *Scan0_p0 = GetVarlieldPtr((record_t*)Scan0,1,4);
                    // Copy from VarChar to VarChar
                    lenScan0_p0 = *((vlen_t*) (Scan0_p0));
                     BytewiseMemcpy(Return7->f0,Scan0_p0,1enScan0_p0);
                     *((vlen_t*)Return7->f0) = lenScan0_p0 ;
                Return7Pos = ((char *) (Return7->f0)) + ALIGN_VARLENS(lenScan0_p0);
                uint16 lenScan0_p1;
                    void *Scan0_p1 = Temp2->f0;
                    // Copy from VarChar to VarChar
                    lenScan0_p1 = *((vlen_t*) (Scan0_p1));
                     BytewiseMemcpy(Return7Pos,Scan0_p1,lenScan0_p1);
                     *((vlen_t*)Return7Pos) = lenScan0_p1
                Return7Pos += ALIGN_VARLENS(lenScan0_p1);
                uint16 lenScan0_p11;
                    void *Scan0_p11 = GetVarFieldPtr((record_t*)BlastOutRec,17,184);
sliceAndDiceBlob(Scan0_p11,(record_t**)&Return7,&Return7Pos,tReturn7,0,&block7,node7,ret
urnNewBlockFunc,0);
                lenScan0_p11 = 0;
                if ( lenScan0_p11 )
                    Return7Pos += ALIGN_VARLENS(lenScan0_p11);
                uint16 lenScan0_p12;
                    void *Scan0_p12 = GetVarFieldPtr((record_t*)BlastOutRec,18,184);
sliceAndDiceBlob(Scan0_p12,(record_t**)&12eturn7,&Return7Pos,tReturn7,0,&block7,node7,ret
urnNewBlockFunc,0);
                lenScan0_p12 = 0;
                if ( lenScan0_p12 )
                    Return7Pos += ALIGN_VARLENS(lenScan0_p12);
                uint16 lenScan0_p13;
                    void *Scan0_p13 = GetVarFieldPtr((record_t*)BlastOutRec,19,184);
sliceAndDiceBlob(Scan0_p13,(record_t**)&Return7,&Return7Pos,tReturn7,0,&block7,node7,ret
urnNewBlockFunc,0);
                lenScan0_p13 = 0;
                if ( lenScan0_p13 )
                    Return7Pos += ALIGN_VARLENS(lenScan0_p13);
                Return7->size = ALIGN_RECORDS((uint8 *)Return7Pos - (uint8*)Return7
- 0);
                // lock record in
                UPDATE_WRITE_ADDR(block7,Return7->size);
            )
          )
        )
      )
   endLoop_Scan0:)
        if ( lastCall )
            deleteTable ( (TDropTableNode(*)plan->m_nodeArray [4]) ;
        if ( lastCall )
            deleteTable ( (TDropTableNode(*)plan->m_nodeArray [5]) ;
        if ( lastCall )
            deleteTable ( (TDropTableNode(*)plan->m_nodeArray[6]) ;
    if (lastCall) node7->returnNewBlock (lastCall) ;
    )
```

Disk-Based Looping Options PIM

Given the differences between the Blast join and other relational joins, the disk-based version of the Blast join is a logical extension to the memory version.

The join becomes "disk-based" when the inner table does not fit in memory. As described above, the inner table can be either the needles or the haystack in the PIM. In the PIM, the size of the inner table is detected before the detailed execution plan is assembled and thus the plan itself is different for disk-based joins. Other designs may use a single algorithm that assumes disk-based joining, but the tradeoff for the simplicity is the attendant performance cost of more subroutine calls and indirection.

For disk-based Blast joins in the PIM, the haystack is the inner table, the programs loops are set up such that a "convenient" number of needle contexts are kept in memory at any given time, where convenient is a function of available memory. This differs from the memory based join where a single needle is compared to each of the haystack records before proceeding to the next needle record.

For each of these needle context groups, the databases reads all of the haystack records from the disk and performs the join against all of the needle records in the context group. It then moves on to the next needle-context group, repeating the reading of the haystack records, and so on. With this algorithm, the number of times the inner table needs to be read from the disk is defined by the formula "numberOfPasses=numberOfInnerGroups/sizeOfEachInnerGroup".

The needle records can instead be the inner table, but this would require that the per-needle Blast state be written to the disk each time after the needle (or group of needles) was processed.

Detailed Implementation of the Interface to the Blast Algorithm

As described in the previous section, the generated code calls the blastAway( ) function for each needle/haystack pair. The blastAway( ) function is principally an interface layer to the underlying sequence analysis algorithm (NCBI Blast). In other words, the blastAwayO function calls the NCBI library functions. All of this is performed within the SPU as ordinary subroutine calls.

The blastAway( ) function (with the "needle-outer" looping convention shown) creates a new "needle-context" object each time the outer looper sequences to the next needle. This is detected by blastAwaysO's second argument being zero (0). The needle-context object is used for all subsequent compares and is destroyed after processing the last haystack record.

Note that with the NCBI Blast, the tBlastOut2 table only loaded on the last haystack record for a given needle record. This is because certain values in the return set can only be computed after all of the haystack values have been processed. In a join where the fields to be returned don't include these "full-set-required" fields, the blastAway( ) function loads the tBlastOut2 table during each haystack processing point.

In this full-set-required case, the outer record pointer (Temp2 in the example code) cannot be used as originally set in the outer looper. To do so would have all of the subsequent query operations use the fields from only the last out record, rather than the outer record corresponding to the HSP. Therefore, the HSP record (BlastOut2) includes an outer-record identifier—in this case a simple pointer in field "BlastOut2->f55" that points to the original outer record. In the disk-based blast join, this is a cache-area identifier that can be translated into a pointer to a copy of the outer record (or relevant subfields thereof), or the means to obtain the outer record (or subfields) off the disk. Since multiple threads can be concurrently executing different Blast joins, all query state information is held in thread-safe storage associated with each thread.

Return Set Psuedo-Fields in PIM

To ease transition for users from "standalone" Blast programs to SQL-Blast, the names of the return fields from the Blast join are similar to the "blastall" program with the "-m7" command line option, which produces XML output. See the http://www.ncbi.nih.gov for complete information on "blastall".

In the XML style, the returned data is somewhat hierarchical, where the highest level of the hierarchy describes the program attributes, like "name", "version" and so on. At the next level, there is the per-query sequence iteration. Next comes the query-subject "hit" information and finally, at the lowest level at the HSPs (high scoring pairs). In the invention, the relevant values from each level are all part of result record's psuedo-fields. Thus, all result records contain the same value in their "blast_program" psuedo-field. Likewise, all of the "hit" information is the same for a related set of HSPs.

The following psuedo-fields (shown with sample values) are enabled:

```
blast_program         | blastn
blast_version         | blastn 2.2.6 [Apr-09-2003]
blast_reference       | -Reference: Altschul, Stephen F., ...
blast_query_len       | 36
hit_num               | 1
hit_len               | 36
hsp_num               | 1
hsp_bit_score         | 71.857743970718
hsp_score             | 36
hsp_evalue            | 4.1295258930225e-19
hsp_query_from        | 1
hsp_query_to          | 36
hsp_hit_from          | 1
hsp_hit_to            | 36
hsp_query_frame       | 1
hsp_hit_frame         | 1
hsp_identity          | 36
```

-continued

| | |
|---|---|
| hsp_positive | 36 |
| hsp_gaps | 0 |
| hsp_align_len | 36 |
| hsp_density | 0 |
| hsp_qseg | ACGTAACCGGTTAAACCCGGGTTTAACCGGTTACGT |
| hsp_hseq | ACGTAACCGGTTAAACCCGGGTTTAACCGGTTACGT |
| hsp_midline | \|\|\|\|\|\|\|\|\|\|\|\|\|\|\|\|\|\|\|\|\|\|\|\|\|\|\|\|\|\|\|\|\|\|\|\| |
| parameters_matrix | tbd |
| parameters_expect | tbd |
| parameters_include | tbd |
| parameters_sc_match | tbd |
| parameters_sc_mismatch | tbd |
| parameters_gap_open | tbd |
| parameters_gap_extend | tbd |
| parameters_filter | tbd |
| parameters_pattern | tbd |
| parameters_entrez_query | tbd |
| hsp_pattern_from | tbd |
| hsp_pattern_to | tbd |
| statistics_db_num | tbd |
| statistics_db_len | tbd |
| statistics_hsp_len | tbd |
| statistics_eff_space | tbd |
| statistics_kappa | tbd |
| statistics_lambda | tbd |
| statistics_entropy | tbd |

The following exist as part of XML, but are not be directly supported by in the PIM because (A) the information is NCBI formatdb' specific and is otherwise present in the information fields of PIM records or (B) they are associated with "megablast" iteration numbers whereas PIM iterations are denoted/documented via the information fields of your records.

blast_db
blast_query_id
blast_query_def
blast_query_seq
iteration_iter_num
iteration_query_id
iteration_query_def
iteration_query_len
iteration_message
hit_id
hit_def
hit_accession The PIM datatypes of the supported psuedo-fields are as follows:

| | |
|---|---|
| blast_program | varchar(20) |
| blast_version | varchar(100) |
| blast_reference | varchar(500) |
| blast_query_len | int4 |
| parameters_matrix | varchar(100) |
| parameters_expect | float8 |
| parameters_include | float8 |
| parameters_sc_match | int4 |
| parameters_sc_mismatch | int4 |
| parameters_gap_open | int4 |
| parameters_gap_extend | int4 |
| parameters_filter | text |
| parameters_pattern | text |
| parameters_entrez_query | text |
| hit_num | int4 |
| hit_len | int4 |
| hsp_num | int4 |
| hsp_bit_score | float8 |
| hsp_score | float8 |
| hsp_evalue | float8 |
| hsp_query_from | int4 |

-continued

| | |
|---|---|
| hsp_query_to | int4 |
| hsp_hit_from | int4 |
| hsp_hit_to | int4 |
| hsp_pattern_from | int4 |
| hsp_pattern_to | int4 |
| hsp_query_frame | int4 |
| hsp_hit_frame | int4 |
| hsp_identity | int4 |
| hsp_positive | int4 |
| hsp_gaps | int4 |
| hsp_align_len | int4 |
| hsp_density | int4 |
| hsp_gseq | text |
| hsp_hseq | text |
| hsp_midline | text |
| statistics_db_num | int4 |
| statistics_db_len | int4 |
| statistics_hsp_len | int4 |
| statistics_eff_space | float8 |
| statistics_kappa | float8 |
| statistics_ lambda | float8 |
| statistics_entropy | float8 |

Storage Method

The logical hierarchy of the PIM file system is field->record->block. In the PIM, max field is 32K, the max record size is 64K. In the PIM, we currently use a blocksize of 128 Kb for all tables, although the design allows this to be per-table.

This section of this document freely interchanges the words BLOB, CLOB and the subtypes of "text", "sequence", "protein", "DNA", "amino acids", and "nucleotides". All are stored in the same manner. The only difference is that BLOBs do not normally have any database functions that operate on them (except perhaps for "length" and conversion to other types). The terms "CLOB" (and "text" in the PIM) describe character sequences that can be operated upon by standard database text operators, like string concatenation. Note, though, that within the BLOB/CLOB content area described below, the "protein" and "nucleotide" data types in the PIM include additional specific header and trailer information, as needed for processing by the Blast algorithm with minimal data conversions.

In implementations other than the current PIM, the sequence CLOBs can be stored using a separate file system on the disk that would hold the CLOB content. A CLOB record field would just be a pointer to the data in the CLOB content partition. This model assumes that CLOBs do not actively participate in the scan, most notably the "where" clause. It likewise assumes that the return set isn't extracted from the CLOB.

The basic scheme in the PIM is 64 KB is the maximum physical record size, but that CLOBs can be represented as part of a logical record that spans multiple physical records. In the following description, the term "record" is used to mean physical record. A 100 Kb CLOB will begin in the "initial" record after the "normal" fixed length and varchar fields. It will continue across subsequent "follower" (also called "extension") records.

If there is a null-bits vector (not shown) for this logical record, all of the null-bits are presented in the initial record only. No null-bits are present in any of the extension records.

Figure 6:
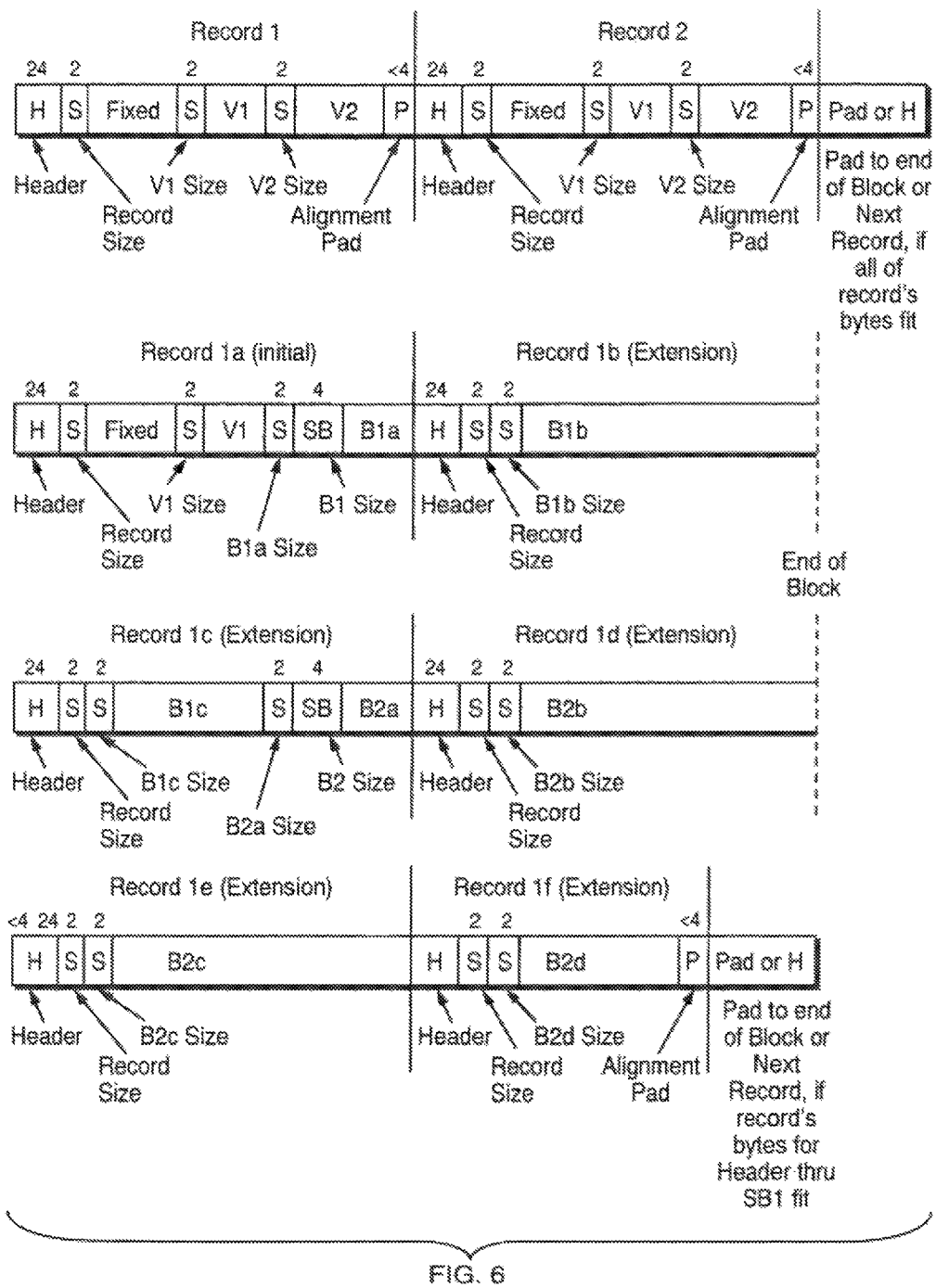
FIG. 6 is a diagram of the preferred record formats.

Referring now to FIG. 6, all CLOB-containing records, both initial and extension, just as varchar-containing records, shall begin with a two-byte size word. On disk, any optional control fields such as TxCreator/TxDeleter/RowId header precede this size word. Such control fields may be useful for controlling visibility in a multi-version database scheme (TxCreator/TxDeleter), or for establishing object identity (RowId), or for other database management purposes that are not directly related to this invention.

As with varchar fields, the first two bytes of the CLOB field define the size, but only for the portion of the CLOB that is present in the containing record.

The first four bytes of the content area contain the total CLOB size. If the CLOB fits in the balance of the record, the size words will be the same, excluding their own sizes.

For records containing CLOBs that require extension records, the extension records, as described above continue to begin with a size word and optional header (for optional control fields described above), but the first field is CLOB continuation material, again including a two-byte size word that describes how much of this continuation material is present in this extension record. All of the record headers in the extension records have exactly the same content (including rowid) as the initial record.

Records and extension records are allowed to contain multiple CLOB fields. In this circumstance, the subsequent CLOB fields begin where the first CLOB field ends, each with their own contained initial-4-byte size and segmented 2-byte size words.

Part of the purpose of this is to maintain consistency between the format of logical records containing CLOBs spanning extension records, and the format of records with no associated extension records. Using the approach described, each record (both initial and extension) meets common format requirements, but a table can now contain records with non-homogenous number of fields.

During query processing, the CLOB, if projected-in, shall appear in memory in a fully contiguous manner. The record header material will never appear for the extension records—if the query projects optional control fields such as the rowid or transaction ids, they only appear for the lead record.

CLOBS are plumbed thru the ODBC connection to continue to provide a single, uniform interface into the PIM.

For users where a high percentage of their queries do not require the CLOB content in the 'where' clause, the PIM will automatically create a projected materialized view that contains the non-CLOB fields. The query planner/optimizer will be able to choose to scan the thin table and separately fetch-and-append the CLOBs.

The CLOBs can also be stored in a separate table (vertical partitioning) where the base table has pointers into the CLOB table and the user's query is automatically converted to the appropriate join. The system can make this storage determination based on explicit user preferences or by automatically changing the storage scheme based on previous query history.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for sequence analysis comprising:
at least one processor configured to:
store at least one subject sequence as a relation in a first data object of a relational database;
determine an instruction execution plan for an instruction of a query language associated with an operation of the relational database that performs a comparison of at least one relational query sequence within a second data object of the relational database against the at least one relational subject sequence within the first data object, the instruction execution plan having a first part that comprises at least one relational database operation that uses the at least one relational query sequence of the second data object and a third data object of the relational database comprising controls, and the instruction execution plan also having a subsequent part that comprises at least one relational database operation including a JOIN operation, such that the instruction execution plan has multiple parts and includes steps for evaluating data in one or more sequences to determine which of the subject sequence or query sequence is to be specified as an inner table or outer table for the JOIN operation;
execute the at least one relational database operation in the first part of the instruction execution plan;
store a data output result relation of execution of the first part of the instruction execution plan as a database relation in the relational database;
use the data output result relation of execution of the first part of the instruction execution plan and the at least one subject sequence of the first data object as at least two data inputs to the at least one relational database operation in the subsequent part of the plan; and
execute the at least one relational database operation in the subsequent part of the plan to complete the comparison.

2. The system as in claim 1, wherein the at least one processor includes multiple processing units, and wherein the instruction execution plan further specifies which instructions in the instruction execution plan are to be distributed to designated ones of the processing units for execution.

3. The system as in claim 2, wherein the instruction execution plan parts are realized as a set of relational database query-specific instruction statements that are compiled and dynamically bound to the processing units at execution time.

4. The system as in claim 1, wherein the subsequent part of the instruction execution plan includes a further relational database operation selected from a group consisting of SORT, AGGREGATE, SCAN, PROJECT, and RESTRICT.

5. The system as in claim 1, wherein the relational database operation in the first part of the instruction execution plan includes a SELECT operation.

6. The system as in claim 1, wherein the sequences represent data selected from a group consisting of nucleic acid, amino acid, and protein identifiers.

7. The system as in claim 1, wherein neither the subject sequence nor the query sequence are stored as a static materialized relational database definition.

8. The system as in claim 1, wherein the comparison operation carried out by the plan determines a degree of similarity of the at least one query sequence to a portion of the at least one subject sequence.

9. The system as in claim 1, wherein the instruction execution plan specifies streaming operations, coupled with tuple set operations, to compare the query sequence against the subject sequence for optimizing performance.

10. The system as in claim 1, wherein the at least one relational database operation of the first part of the instruction execution plan comprises a cross-product join of a control table and the at least one query sequence, and the at least one relational database operation of the second part of the instruction execution plan comprises a join of the resultant cross-product join of the first part of the instruction plan and the at least one subject sequence to produce a result set.

11. A computer program product for sequence analysis, the computer program product comprising a non-transitory computer readable storage medium having program instructions embodied therewith, the program instructions executable by at least one processor to cause the at least one processor to:
store at least one subject sequence as a relation in a first data object of a relational database;
determine an instruction execution plan for an instruction of a query language associated with an operation of the relational database that performs a comparison of at least one relational query sequence within a second data object of the relational database against the at least one relational subject sequence within the first data object, the instruction execution plan having a first part that comprises at least one relational database operation that uses the at least one relational query sequence of the second data object and a third data object of the relational database comprising controls, and the instruction execution plan also having a subsequent part that comprises at least one relational database operation including a JOIN operation, such that the instruction execution plan has multiple parts and includes steps for evaluating data in one or more sequences to determine which of the subject sequence or query sequence is to be specified as an inner table or outer table for the JOIN operation;
execute the at least one relational database operation in the first part of the instruction execution plan;
store a data output result relation of execution of the first part of the instruction execution plan as a database relation in the relational database;
use the data output result relation of execution of the first part of the instruction execution plan and the at least one subject sequence of the first data object as at least two data inputs to the at least one relational database operation in the subsequent part of the plan; and
execute the at least one relational database operation in the subsequent part of the plan to complete the comparison.

12. The computer program product as in claim 11, wherein the at least one processor includes multiple processing units, and wherein the instruction execution plan further specifies which instructions in the instruction execution plan are to be distributed to designated ones of the processing units for execution.

13. The computer program product as in claim 12, wherein the instruction execution plan parts are realized as a set of relational database query-specific instruction statements that are compiled and dynamically bound to the processing units at execution time.

14. The computer program product as in claim 11, wherein the subsequent part of the instruction execution plan includes a further relational database operation selected from a group consisting of SORT, AGGREGATE, SCAN, PROJECT, and RESTRICT.

15. The computer program product as in claim 11, wherein the relational database operation in the first part of the instruction execution plan includes a SELECT operation.

16. The computer program product as in claim 11, wherein the sequences represent data selected from a group consisting of nucleic acid, amino acid, and protein identifiers.

17. The computer program product as in claim 11, wherein neither the subject sequence nor the query sequence are stored as a static materialized relational database definition.

18. The computer program product as in claim 11, wherein the comparison operation carried out by the plan determines a degree of similarity of the at least one query sequence to a portion of the at least one subject sequence.

19. The computer program product as in claim 11, wherein the instruction execution plan specifies streaming operations, coupled with tuple set operations, to compare the query sequence against the subject sequence for optimizing performance.

20. The computer program product as in claim 11, wherein the at least one relational database operation of the first part of the instruction execution plan comprises a cross-product join of a control table and the at least one query sequence, and the at least one relational database operation of the second part of the instruction execution plan comprises a join of the resultant cross-product join of the first part of the instruction plan and the at least one subject sequence to produce a result set.

* * * * *